United States Patent
Demetriades et al.

(10) Patent No.: US 10,631,564 B2
(45) Date of Patent: Apr. 28, 2020

(54) ENTERICALLY COATED MICROPARTICLE COMPOSITIONS AND METHODS FOR MODIFIED NUTRIENT DELIVERY

(71) Applicant: University of Southern California, Los Angeles, CA (US)

(72) Inventors: Elizabeth Demetriades, Los Angeles, CA (US); Travis Williams, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/737,257

(22) PCT Filed: Jun. 17, 2016

(86) PCT No.: PCT/US2016/038244
§ 371 (c)(1),
(2) Date: Dec. 15, 2017

(87) PCT Pub. No.: WO2016/205754
PCT Pub. Date: Dec. 22, 2016

(65) Prior Publication Data
US 2018/0168216 A1    Jun. 21, 2018

Related U.S. Application Data

(60) Provisional application No. 62/182,366, filed on Jun. 19, 2015.

(51) Int. Cl.
*A23P 10/30*        (2016.01)
*A23P 20/10*        (2016.01)
(Continued)

(52) U.S. Cl.
CPC ............. *A23P 10/30* (2016.08); *A23L 33/125* (2016.08); *A23L 33/17* (2016.08); *A23L 33/185* (2016.08);
(Continued)

(58) Field of Classification Search
CPC .......... A23P 10/30; A23P 10/40; A23L 33/19; A23L 33/125; A23L 33/18; A23L 33/30; A23L 33/40; A23L 33/17; A23L 20/10
See application file for complete search history.

(56) References Cited

U.S. PATENT DOCUMENTS

| | | | |
|---|---|---|---|
| 4,134,405 | A | 1/1979 | Smit |
| 4,166,452 | A | 9/1979 | Generales, Jr. |

(Continued)

FOREIGN PATENT DOCUMENTS

| | | | |
|---|---|---|---|
| CA | 2377502 | A1 | 1/2001 |
| CA | 2897448 | A1 | 7/2014 |

(Continued)

OTHER PUBLICATIONS

Czarnocka et al, Gastro-Resistant Characteristics of GRAS-Grade Enteric Coatings for Pharmaceutical and Nutraceutical products,International Journal of Pharmaceutics 486(1-2) • Mar. 2015 with 196 Reads DOI: 10.1016/j.ijpharm.2015.03.039 • (Year: 2015).*

(Continued)

*Primary Examiner* — Carlos A Azpuru
(74) *Attorney, Agent, or Firm* — Foley & Lardner LLP; Antoinette F. Konski; Peter Diez

(57) ABSTRACT

This disclosure provides a microencapsulated capsule or microparticle comprising a nutrient-filled core encapsulated in an enteric coating. The microparticles are useful in the treatment of a variety of disorders when ingested or administered to a subject in need thereof. Alternate non-encapsu- (Continued)

lated methods and compositions for providing the desired intestinal release are provided included modified nutrient composition and matrix embedded nutrient.

11 Claims, 10 Drawing Sheets

(51) Int. Cl.
    *A23L 33/185*     (2016.01)
    *A23L 33/17*     (2016.01)
    *A23L 33/00*     (2016.01)
    *A23L 33/19*     (2016.01)
    *A23L 33/125*     (2016.01)
    *A23P 10/40*     (2016.01)

(52) U.S. Cl.
    CPC ............... *A23L 33/19* (2016.08); *A23L 33/30* (2016.08); *A23L 33/40* (2016.08); *A23P 10/40* (2016.08); *A23P 20/10* (2016.08); *A23V 2002/00* (2013.01)

(56) References Cited

U.S. PATENT DOCUMENTS

| | | | |
|---|---|---|---|
| 4,256,108 A | 3/1981 | Theeuwes |
| 4,265,874 A | 5/1981 | Bonsen et al. |
| 4,900,306 A | 2/1990 | Quinn et al. |
| 5,026,559 A | 6/1991 | Eichel et al. |
| 5,322,697 A | 6/1994 | Meyer |
| 5,360,614 A | 11/1994 | Fox et al. |
| 5,470,839 A | 11/1995 | Laughlin et al. |
| 5,536,156 A | 7/1996 | Fox et al. |
| 5,545,410 A | 8/1996 | Fox et al. |
| 5,576,306 A | 11/1996 | Dressman et al. |
| 5,611,787 A | 3/1997 | Demeter et al. |
| 5,753,253 A | 5/1998 | Meyer |
| 5,776,887 A | 7/1998 | Wibert et al. |
| 5,811,388 A | 9/1998 | Friend et al. |
| 5,977,175 A | 11/1999 | Lin |
| 5,998,363 A | 12/1999 | Forse et al. |
| 6,103,269 A | 8/2000 | Wunderlich et al. |
| 6,143,786 A | 11/2000 | Gohman et al. |
| 6,248,375 B1 | 6/2001 | Gilles et al. |
| 6,248,390 B1 | 6/2001 | Stillman |
| 6,267,988 B1 | 7/2001 | Meyer |
| 6,420,350 B1 | 7/2002 | Fleischner |
| 6,558,690 B2 | 5/2003 | Portman |
| 6,558,708 B1 | 5/2003 | Lin |
| 6,569,463 B2 | 5/2003 | Patel et al. |
| 6,624,210 B1 | 9/2003 | Petereit et al. |
| 6,716,815 B2 | 4/2004 | Portman |
| 6,770,620 B2 | 8/2004 | Henriksen |
| 6,774,111 B1 | 8/2004 | Wolf et al. |
| 6,809,115 B2 | 10/2004 | Katz et al. |
| 6,846,891 B2 | 1/2005 | Petereit et al. |
| 7,025,791 B2 | 4/2006 | Levine et al. |
| 7,037,344 B2 | 5/2006 | Kagan et al. |
| 7,048,906 B2 | 5/2006 | Lin et al. |
| 7,081,239 B2 | 7/2006 | Lin |
| 7,122,058 B2 | 10/2006 | Levine et al. |
| 7,157,100 B2 | 1/2007 | Doshi et al. |
| 7,169,416 B2 | 1/2007 | Koss et al. |
| 7,347,875 B2 | 3/2008 | Levine et al. |
| 7,641,924 B2 | 1/2010 | Mizumoto et al. |
| 7,670,627 B2 | 3/2010 | Shefer et al. |
| 7,718,194 B2 | 5/2010 | Chenevier et al. |
| 7,766,861 B2 | 8/2010 | Levine et al. |
| 7,785,291 B2 | 8/2010 | Marco et al. |
| 7,794,447 B2 | 9/2010 | Dann et al. |
| 7,815,947 B2 | 10/2010 | Mizumoto et al. |
| 7,935,073 B2 | 5/2011 | Levine et al. |
| 8,226,602 B2 | 7/2012 | Quijana et al. |
| 8,486,153 B2 | 7/2013 | Levine et al. |
| 8,586,103 B2 | 11/2013 | Li et al. |
| 8,821,429 B2 | 9/2014 | Vargas |
| 8,828,953 B2 | 9/2014 | Baron et al. |
| 8,865,649 B2 | 10/2014 | Hageman |
| 8,882,698 B2 | 11/2014 | Levine et al. |
| 9,060,844 B2 | 6/2015 | Kagan et al. |
| 9,066,536 B2 | 6/2015 | Astrup et al. |
| 2001/0036495 A1 | 11/2001 | Ganan-Calvo |
| 2003/0130346 A1 | 7/2003 | Kuzela et al. |
| 2003/0192552 A1 | 10/2003 | Mongeon |
| 2003/0220413 A1 | 11/2003 | Petereit et al. |
| 2004/0018190 A1 | 1/2004 | Ando et al. |
| 2004/0132819 A1 | 7/2004 | Auestad et al. |
| 2004/0197380 A1 | 10/2004 | Wolf et al. |
| 2004/0234631 A1 | 11/2004 | Hoie |
| 2005/0014345 A1 | 1/2005 | Miyamoto et al. |
| 2005/0038415 A1 | 2/2005 | Rohr et al. |
| 2005/0143459 A1 | 6/2005 | Kuzela et al. |
| 2005/0154064 A1 | 7/2005 | Piomelli et al. |
| 2005/0175763 A1 | 8/2005 | Purpura et al. |
| 2006/0046969 A1 | 3/2006 | Maggio |
| 2006/0141103 A1 | 6/2006 | Heritage et al. |
| 2006/0178560 A1 | 8/2006 | Saadat et al. |
| 2006/0204576 A1 | 9/2006 | Petereit et al. |
| 2007/0198074 A1 | 8/2007 | Dann et al. |
| 2008/0020041 A1 | 1/2008 | Ayres |
| 2009/0011019 A1 | 1/2009 | Jahagirdar et al. |
| 2009/0093767 A1 | 4/2009 | Kelleher |
| 2009/0093839 A1 | 4/2009 | Kelleher |
| 2009/0181109 A1 | 7/2009 | Barker |
| 2009/0252767 A1* | 10/2009 | Durig ............... A61K 9/282 424/400 |
| 2010/0016425 A1 | 1/2010 | Vath |
| 2010/0056948 A1 | 3/2010 | Hornby et al. |
| 2010/0203134 A1 | 8/2010 | Chenevier et al. |
| 2010/0267643 A1 | 10/2010 | Baron et al. |
| 2011/0065660 A1 | 3/2011 | Baron et al. |
| 2011/0076326 A1 | 3/2011 | Caillard et al. |
| 2011/0081400 A1 | 4/2011 | Langford et al. |
| 2011/0117192 A1 | 5/2011 | Navon et al. |
| 2011/0178005 A1 | 7/2011 | Yamka et al. |
| 2011/0217380 A1* | 9/2011 | Geraedts ............... A61K 9/5026 424/489 |
| 2011/0268666 A1 | 11/2011 | Friedman et al. |
| 2011/0268795 A1 | 11/2011 | Fayad |
| 2012/0052151 A1 | 3/2012 | Sannino et al. |
| 2012/0064143 A1* | 3/2012 | Sharp ............... A61K 9/1635 424/439 |
| 2012/0094942 A1 | 4/2012 | Baron et al. |
| 2013/0035559 A1 | 2/2013 | Hornby et al. |
| 2013/0150823 A1 | 6/2013 | Montgomery et al. |
| 2013/0273154 A1 | 10/2013 | Fayad et al. |
| 2013/0337055 A1 | 12/2013 | Schentag et al. |
| 2014/0127299 A1 | 5/2014 | Dordunoo |
| 2014/0127307 A1 | 5/2014 | Venkatesh et al. |
| 2014/0127351 A1 | 5/2014 | Disilvestro |
| 2014/0141082 A1 | 5/2014 | Gao |
| 2014/0193498 A1 | 7/2014 | Baron et al. |
| 2014/0194805 A1 | 7/2014 | Levine et al. |
| 2014/0294951 A1 | 10/2014 | Fayad et al. |
| 2014/0377353 A1 | 12/2014 | Borges De Brito |
| 2015/0038453 A1 | 2/2015 | Hageman |
| 2015/0038583 A9 | 2/2015 | Kabaradjian |
| 2015/0118298 A1 | 4/2015 | Zhang et al. |
| 2015/0150894 A1 | 6/2015 | Baron et al. |
| 2015/0173405 A1 | 6/2015 | Van Der Beek et al. |
| 2015/0230510 A1 | 8/2015 | Navia et al. |
| 2015/0306128 A1 | 10/2015 | Armstrong |
| 2015/0320817 A1 | 11/2015 | Astrup et al. |
| 2018/0168216 A1 | 6/2018 | Demetriades et al. |

FOREIGN PATENT DOCUMENTS

| | | |
|---|---|---|
| CA | 2899220 A1 | 8/2014 |
| CN | 1555729 A | 12/2004 |
| CN | 101125132 A | 2/2008 |
| CN | 101223987 A | 7/2008 |
| CN | 102935106 A | 2/2013 |
| CN | 103211148 A | 7/2013 |

(56) References Cited

FOREIGN PATENT DOCUMENTS

| | | |
|---|---|---|
| CN | 103284275 A | 9/2013 |
| CN | 103300374 A | 9/2013 |
| CN | 103385469 A | 11/2013 |
| CN | 103416801 A | 12/2013 |
| CN | 103584083 A | 2/2014 |
| CN | 103652862 A | 3/2014 |
| CN | 103719756 A | 4/2014 |
| CN | 103750338 A | 4/2014 |
| CN | 103766870 A | 5/2014 |
| CN | 104107188 A | 10/2014 |
| CN | 103478792 B | 12/2014 |
| CN | 104187670 A | 12/2014 |
| CN | 104286849 A | 1/2015 |
| CN | 104305206 A | 1/2015 |
| CN | 104623097 A | 5/2015 |
| CN | 104856059 A | 8/2015 |
| EP | 0 724 842 A2 | 8/1996 |
| EP | 0 898 900 A2 | 3/1999 |
| EP | 1 129 711 A2 | 9/2001 |
| EP | 1 371 368 A1 | 12/2003 |
| EP | 1 143 988 B1 | 2/2004 |
| EP | 1 513 541 B1 | 1/2009 |
| EP | 2 085 089 A1 | 8/2009 |
| WO | WO-2011/059672 A2 | 5/2011 |
| WO | WO-2012/055577 A1 | 5/2012 |
| WO | WO-2014/134225 A2 | 9/2014 |
| WO | WO-2014/197632 A2 | 12/2014 |
| WO | WO-2014/204382 A1 | 12/2014 |
| WO | WO-2015/063038 A1 | 5/2015 |
| WO | WO-2015/085010 A1 | 6/2015 |
| WO | WO-2015/086467 A1 | 6/2015 |
| WO | WO-2015/120471 A1 | 8/2015 |
| WO | WO-2015/140798 A2 | 9/2015 |
| WO | WO-2016/205701 A1 | 12/2016 |
| WO | WO-2016/205754 A1 | 12/2016 |

OTHER PUBLICATIONS

Ackerman M H et al. (2006), "Technologic approaches to determining proper placement of enteral feeding tubes", AACN Adv Crit Care, 17(3):246-249.

American Diabetes Association (2013), "Economic costs of diabetes in the U.S. in 2012", Diabetes Care, 36(4): 1033-1046.

Aron-Wisnewsky J et al. (2012), "The importance of the gut microbiota after bariatric surgery", Nat Rev Gastroenterol Hepatol., 9(10): 590-598.

Ashrafian H et al. (2011), "Diabetes resolution and hyperinsulinaemia after metabolic Roux-en-Y gastric bypass", obesity reviews, 12(5): e257-e272.

Aspire Bariatrics—AspireAssist Non-Surgical Weight Loss, http://www.aspirebariatrics.com/, retrieved on Aug. 10, 2016.

Beckman L M et al. (2011), "Changes in gastrointestinal hormones and leptin after Roux-en-Y gastric bypass surgery", JPEN J Parenter Enteral Nutr., 35(2):169-180.

Beglinger S et al. (2010), "Role of fat hydrolysis in regulating glucagon-like Peptide-1 secretion", J Clin Endocrinol Metab., 95(2): 879-886.

Bosi E (2010), "Time for testing incretin therapies in early type 1 diabetes?", J Clin Endocrinol Metab., 95(6): 2607-2609.

Bradley D et al. (2012), "Effects of bariatric surgery on glucose homeostasis and type 2 diabetes", Gastroenterology, 143(4):897-912.

Bray G A (2016), "Obesity in adults: Health hazards", In: UpToDate, Martin KS (Dep Ed), UpToDate, Waltham, MA (Accessed on Aug. 12, 2016).

Buchwald H et al. (2004), "Bariatric surgery: a systematic review and meta-analysis", JAMA, 292(14): 1724-1737.

Chaikomin R et al. (2008), "Effects of mid-jejunal compared to duodenal glucose infusion on peptide hormone release and appetite in healthy men", Regul Pept., 150(1-3): 38-42.

ClinicalTrials.gov, "Levodopa-Carbidopa Intestinal Gel Open-Label Study in Advanced Parkinson's Disease", Retrieved from http://clinicaltrials.gov/ct2/sho/NCT00335153 in Aug. 2016.

ClinicalTrials.gov, "The Role of the Duodenum in the Pathogenesis of Insulin Resistance and Type 2 Diabetes Mellitus", Retrieved from http://clinicaltrials.gov/ct2/show/NCT00568620?term=enteraltube &rank=52 on Aug. 10, 2016.

Colditz G A et al. (1995), "Weight gain as a risk factor for clinical diabetes mellitus in women", Ann Intern Med., 122(7):481-486.

Cook Medical, https://www.cookmedical.com/products/cc_njft_webds/, Retrieved in Aug. 2016.

Cortrak Enteral Access System, http://www.corpakmedsystems.com/cortrak-product-page/cortrak/, Retrieved on Aug. 11, 2016.

Czupryniak L et al. (2010), "Long-term results of gastric bypass surgery in morbidly obese type 1 diabetes patients", Obes Surg., 20(4): 506-508.

De Jonge C et al. (2011), "Endobarrier (TM) Gastrointestinal Liner Treatment Rapidly Improves Diabetes Parameters Paralleled by Increased Postprandial GLP-1 and PYY Levels in Obese Type 2 Diabetic Patients", Poster 83 Poster Sessions and Abstract Book 2nd World Congress on Interventional Therapies for Type 2 Diabetes Poster Presentation in Conference Proceedings, New York Mar. 2011.

Deane A M et al. (2009), "Evaluation of a bedside technique for postpyloric placement of feeding catheters", Crit Care Resusc., 11(3):180-183.

Dirksen C et al. (2010), "Postprandial diabetic glucose tolerance is normalized by gastric bypass feeding as opposed to gastric feeding and is associated with exaggerated GLP-1 secretion: a case report", Diabetes Care, 33(2): 375-377.

DuoDopa, https://www.duopa.com, Retrieved in Aug. 2016.

Elcelyx Pipeline, Retrieved from http://elcelyx.com/clinical/metformin-dr/ on Aug. 11, 2016.

Elcelyx Therapeutics (2012), "Elcelyx' Lovidia ingredient promotes satiety", Retrieved from http://newhope.com/specialty/elcelyx-lovidia-ingredient-promotes-satiety on Aug. 11, 2016.

EndoBarrier Overview, http://www.gidynamics.com/endobarrier-overview.php, retrieved on Aug. 10, 2016.

EndoSphere, http://www.endosphereinc.com/, retrieved on Aug. 10, 2016.

Falken Y et al. (2011), "Changes in glucose homeostasis after Roux-en-Y gastric bypass surgery for obesity at day three, two months, and one year after surgery: role of gut peptides", J Clin Endocrinol Metab., 96(7):2227-2235.

Flegal K M et al. (2012), "Prevalence of obesity and trends in the distribution of body mass index among US adults, 1999-2010", JAMA, 307(5):491-497.

FoodBev Media, "Alain Baron on weight management and satiety", Posted by Shaun Weston on Nov. 5, 2012, Retrieved from http://www.foodbev.com/news/alain-baron-on-weight-management-and-sat/ on Aug. 11, 2016.

Foster-Schubert K E et al. (2008), "Acyl and total ghrelin are suppressed strongly by ingested proteins, weakly by lipids, and biphasically by carbohydrates", J Clin Endocrinol Metab., 93(5):1971-1979.

Galera S C et al. (2010), "The safety of oral use of L-glutamine in middle-aged and elderly individuals", Nutrition, 26(4):375-381.

Gaylinn B D et al. (2010), "Luminal influences to orchestrate gastroenterological hormone secretion: the fat, long-chain Fatty Acid, cholecystokinin, glucagon-like Peptide 1 axis", J Clin Endocrinol Metab., 95(2):503-504.

Geraedts M C et al. (2011), "Intraduodenal administration of intact pea protein effectively reduces food intake in both lean and obese male subjects", PLoS One. 2011, 6(9):e24878.

Gray R et al. (2007), "Bedside electromagnetic-guided feeding tube placement: an improvement over traditional placement technique?", Nutr Clin Pract., 22(4):436-444.

Greenfield J R et al. (2009), "Oral glutamine increases circulating glucagon-like peptide 1, glucagon, and insulin concentrations in lean, obese, and type 2 diabetic subjects", Am J Clin Nutr., 89(1):106-113.

Hall K D et al. (2011), "Quantification of the effect of energy imbalance on bodyweight", Lancet, 378(9793): 826-837.

(56) References Cited

OTHER PUBLICATIONS

Hansen E N et al. (2011), "Role of the foregut in the early improvement in glucose tolerance and insulin sensitivity following Roux-en-Y gastric bypass surgery", Am J Physiol Gastrointest Liver Physiol., 300(5): G795-802.
Hansen K B et al. (2011), "2-Oleoyl glycerol is a GPR119 agonist and signals GLP-1 release in humans", J Clin Endocrinol Metab., 96(9): E1409-17.
Holzinger U et al. (2011), "Jejunal tube placement in critically ill patients: A prospective, randomized trial comparing the endoscopic technique with the electromagnetically visualized method", Crit Care Med., 39(1):73-77.
International Preliminary Report on Patentability dated Dec. 28, 2017, from application No. PCT/US2016/038159.
International Preliminary Report on Patentability dated Dec. 28, 2017, from application No. PCT/US2016/038244.
International Search Report and Written Opinion dated Oct. 28, 2016, from application No. PCT/US2016/038244.
International Search Report and Written Opinion dated Sep. 7, 2016, from application No. PCT/US2016/038159.
Jacobsen S H et al. (2012), "Changes in gastrointestinal hormone responses, insulin sensitivity, and beta-cell function within 2 weeks after gastric bypass in non-diabetic subjects", Obes Surg., 22(7):1084-1096.
Kaushik, N. et al. (2005) "Enteral Feeding Without Pancreatic Stimulation," Pancreas 31(4):353-359.
Kielgast U et al. (2011), "Antidiabetic Actions of Endogenous and Exogenous GLP-1 in Type 1 Diabetic Patients With and Without Residual Beta-Cell Function", Diabetes, vol. 60, pp. 1599-1607.
Kless S et al. (2009), "Has the introduction of an electromagnetic tube placement system reduced Inappropriate parenteral nutrition utilization and associated costs?" Poster, Nutr Clin Pract. 2009, 24(1): Abstract 91.
Koopmann M C et al. (2011), "A team-based protocol and electromagnetic technology eliminate feeding tube placement complications", Ann Surg., 253(2):297-302.
Laferrere B et al. (2008), "Effect of Weight Loss by Gastric Bypass Surgery Versus Hypocaloric Diet on Glucose and Incretin Levels in Patients with Type 2 Diabetes", J Clin Endocrinol Metab, 93(7): 2479-2485.
Layer P et al. (1995), "Ileal release of glucagon-like peptide-1 (GLP-1): Association with inhibition of gastric acid secretion in humans", Dig Dis Sci., 40(5): 1074-1082.
Maahs DM et al. (2010), "Epidemiology of type 1 diabetes", Endocrinol Metab Clin North Am. 2010, 39(3):481-497.
Mackay P et al. (2009), "Corpak with Cortrak" Poster, Presented at Saint Joseph Health System; Jan. 2009; Lexington, KY.
Martins et al. (2009), "Glucose Tolerance in the Proximal Versus the Distal Small Bowel in Wistar Rats", Obes Surg., 19:202-206.
MedGadget (2013), "A Sleeve for Your Small Intestine: Interview with GI Dynamics Founder, Andy Levine", Retrieved from http://www.medgadget.com/2013/04/a-sleeve-for-your-small-intestine-interview-with-gi-dynamics-founder-andy-levine.html on Aug. 16, 2016.
Mendez C E et al. (2010), "Outcomes of Roux-en-Y gastric bypass surgery for severely obese patients with type 1 diabetes: a case series report", Diabetes Metab Syndr Obes., 3:281-283.
Mingrone G et al. (2012), "Bariatric Surgery versus Conventional Medical Therapy for Type 2 Diabetes", N Engl J Med 2012, 366(17):1577-1585.
Muscle Milk 100 Calorie Protein Shake, Retrieved from http://www.cytosport.com/products/muscle-milk/muscle-milk-light-100-calorie-ready-to-drink on Aug. 10, 2016.
Nakatani H et al. (2009), "Serum bile acid along with plasma incretins and serum high-molecular weight adiponectin levels are increased after bariatric surgery", Metabolism, 58(10): 1400-1407.
NIH Conference (1991), "Gastrointestinal surgery for severe obesity. Consensus Development Conference Panel", Ann Intern Med., 115(12):956-961.
Olivan B et al. (2009), "Effect of weight loss by diet or gastric bypass surgery on peptide YY3-36 levels", Ann Surg., 249(6):948-953.
Paniagua J A et al. (2007), "A MUFA-rich diet improves posprandial glucose, lipid and GLP-1 responses in insulin-resistant subjects", J Am Coll Nutr., 26(5):434-444.
Phang J et al. (2006), "Feeding tube placement with the aid of a new electromagnetic transmitter", JPEN J Parenter Enteral Nutr. 2006, 30(2): Abstract S082.
Pournaras D J et al. (2009), "Obesity, gut hormones, and bariatric surgery", World J Surg., 33(10): 1983-1988.
Pournaras D J et al. (2010), "Remission of Type 2 Diabetes after Gastric Bypass and Banding: Mechanisms and 2 Year Outcomes", Annals of Surgery. 2010, 252(6):966-971.
Rothstein R I (2011), "Medical Device Therapy for Obesity and Metabolic Disease—The Current Landscape", Retrieved from http://www.obesitydevices.org/DDOMD%20Session%201/Rothstein1.pdf on Aug. 10, 2016.
Rubino F et al. (2010), "Metabolic Surgery to Treat Type 2 Diabetes: Clinical Outcomes and Mechanisms of Action", Annu Rev Med 2010, 61:393-411.
Samocha-Bonet D et al. (2011), "Glutamine reduces postprandial glycemia and augments the glucagon-like peptide-1 response in type 2 diabetes patients", J Nutr., 141(7):1233-1238.
Schauer P R et al. (2012), "Bariatric Surgery versus Intensive Medical Therapy in Obese Patients with Diabetes", N Engl J Med., 366(17): 1567-1576.
Schouten R et al. (2010), "A multicenter, randomized efficacy study of the EndoBarrier Gastrointestinal Liner for presurgical weight loss prior to bariatric surgery", Ann Surg., 251(2):236-243.
Small C J et al. (2004), "Gut hormones as peripheral anti obesity targets", Abstract, Curr Drug Targets CNS Neurol Disord., 3(5):379-388.
Stefater M A et al. (2012), "All bariatric surgeries are not created equal: insights from mechanistic comparisons", Endocr Rev., 33(4): 595-622.
Stockdale W et al. (2007), "Nasoenteric feeding tube insertion utilizing an electromagnetic tube placement system" Poster, Nutr Clin Pract. 2007, 22:118.
Suarez-Pinzon W L et al. (2011), "Combination therapy with a dipeptidyl peptidase-4 inhibitor and a proton pump inhibitor induces Beta-cell neogenesis from adult human pancreatic duct cells implanted in immunodeficient mice", Cell Transplant, 20(9): 1343-1349.
Sumithran P et al. (2011), "Long-Term Persistence of Hormonal Adaptations to Weight Loss", N Engl J Med 2011, 365(17): 1597-1604.
Taylor S J et al. (2010), "Treating delayed gastric emptying in critical illness: metoclopramide, erythromycin, and bedside (cortrak) nasointestinal tube placement", JPEN J Parenter Enteral Nutr., 34(3):289-294.
Trottier S et al. (2011), "Electromagnetic guided feeding tube insertion: Enhancing patient safety", Poster presentation at: 40th Society of Critical Care Medicine Conference; Jan. 15-19, 2011; San Diego, CA; Abstract 264.
U.S. Final Office Action dated Mar. 13, 2017 in U.S. Appl. No. 13/918,808.
U.S. Final Office Action dated Mar. 21, 2018, from U.S. Appl. No. 13/918,808.
U.S. Non-Final Office Action dated Aug. 21, 2017 in U.S. Appl. No. 13/918,808.
U.S. Non-Final Office Action dated Nov. 9, 2016, from U.S. Appl. No. 13/918,808.
ValenTx—Technology, http://www.valentx.com/technology.php, retrieved on Aug. 10, 2016.
Vantyghem M C et al. (2011), "Diabetes cell therapy: a decade later", Minerva Endocrinol., 36(1): 23-39.
Ward E et al. (2003), "Oral glutamine in paediatric oncology patients: a dose finding study", Eur J Clin Nutr., 57(1):31-36.
Weiner J P et al. (2013), "Impact of Bariatric Surgery on Health Care Costs of Obese Persons: A 6-Year Follow-up of Surgical and Comparison Cohorts Using Health Plan Data", JAMA Surg., 148(6): 555-562.

(56) References Cited

OTHER PUBLICATIONS

Welch, I.M. et al. (1988) "Comparisons of the effects on satiety and eating behavior of infusion of lipid into the different regions of the small intestine," Gut 29:306-311.
Willett W C et al. (1999), "Guidelines for healthy weight", N Engl J Med., 341(6):427-434.
Non-Final Office Action dated May 29, 2019, from U.S. Appl. No. 13/918,808.
Final Office Action dated Oct. 22, 2019, from U.S. Appl. No. 13/918,808.
Non-Final Office Action dated Aug. 8, 2019, from U.S. Appl. No. 15/737,212.
Final Office Action dated Jan. 23, 2020, from U.S. Appl. No. 15/737,212.

* cited by examiner

2.22.16 D+C 160kcal Suglets
2.26.16 D+C 160kcal 50% CC coated Suglets

D UC = ◊  C EC = ○
D EC = ▲  C UC = □

GLUCOSE
2.22.16 D+C 160kcal Suglets
2.26.16 D+C 160kcal 50% CC coated Suglets

Fullness
2.22.16 D+C 160kcal Suglets
2.26.16 D+C 160kcal 50% CC coated Suglets

Nausea
2.22.16 D+C 160kcal Suglets
2.26.16 D+C 160kcal 50% CC coated Suglets

PAIN
2.22.16 D+C 160kcal Suglets
2.26.16 D+C 160kcal 50% CC coated Suglets

2.22.16 D+C 160kcal Suglets
2.26.16 D+C 160kcal 50% CC coated Suglets

D UC = ◇   C EC = ○
D EC = ▲   C UC = ▫

HUNGER
2.22.16 D+C 160kcal Suglets
2.26.16 D+C 160kcal 50% CC coated Suglets

Feels Like Eating
2.22.16 D-C 160kcal Suglets
2.26.16 D+C 160kcal 50% CC coated Suglets

Palpita/ons
2.22.16 D+C 160kcal Suglets
2.26.16 D+C 160kcal 50% CC coated Suglets

Perspiration
2.22.16 D-C 160kcal Suglets
2.26.16 D+C 160kcal 50% CC coated Suglets

ENTERICALLY COATED MICROPARTICLE COMPOSITIONS AND METHODS FOR MODIFIED NUTRIENT DELIVERY

CROSS-REFERENCE TO RELATED APPLICATIONS

This application is a national stage application under 35 U.S.C. § 371 of International Application No. PCT/US2016/038244, filed Jun. 17, 2016, which claims the benefit under 35 U.S.C. § 119(e) of U.S. Provisional Application Ser. No. 62/182,366, filed Jun. 19, 2015, the contents each of which are incorporated by reference into the present disclosure in their entireties.

BACKGROUND

Obesity is the leading cause of the worldwide type 2 diabetes epidemic and many other obesity related disorders. Over eighty percent of type 2 diabetes is attributed to excess weight. Currently, over two-thirds of adults in the United States are overweight or obese, as are about one-and-a-half billion people worldwide. Failure to control obesity underlies the increasing cost of diabetes care which, in the U.S., rose to $245 billion in 2012.

Current standard medical care for obesity and type 2 diabetes and related disorders involves advice to adopt a healthy lifestyle and the prescription of oral and injected medication. These approaches, however, have poor long-term efficacy. The most effective therapy for both obesity and related disorders, including type 2 diabetes, is widely considered to be surgical intervention, such as bariatric surgery, Roux-en-Y gastric bypass and the related sleeve gastrectomy and biliopancreatic diversion. These surgical procedures, particularly gastric bypass surgery, are highly effective at promoting weight loss and controlling type 2 diabetes, with reported drug-free remission of diabetes in 40-90% of patients. However, bariatric surgery is not available to the vast majority of those who could benefit from it worldwide, due to its high cost and medical guidelines which limit its use. In addition, many medically eligible people decline surgery due to concerns about short and long-term risks.

The unmet clinical need is a safe, broadly applicable, low-cost alternative to bariatric surgery for the management of obesity, and related disorders and co-morbidities, including type 2 diabetes mellitus.

While research studies have demonstrated that delivering nutrients directly to the small intestine and bypassing the stomach can increase satiety and reduce subsequent food intake, there is still an unmet need for a safe, effective, broadly applicable, low-cost therapy for achieving direct nutrient delivery to the upper intestine that simulates the benefit of gastric bypass.

SUMMARY

Provided herein is a microencapsulated capsule or "microparticle" comprising, or alternatively consisting essentially of, or yet further consisting of a nutrient-filled core encapsulated in an enteric coating, e.g., that in one aspect comprises, or alternatively consists essentially of, or yet further consists of, a GRAS material.

In some embodiments, the core includes at least one macronutrient and optionally one or more micronutrients, excipients, hydrogels, bile acids, probiotics, and/or preservatives.

In some embodiments, the macronutrients include one or more of a protein, a carbohydrate, and a lipid. In some other embodiments, the macronutrient includes at least one of Ensure®, whole milk power, sucrose, and sugar spheres. In yet some other embodiments, the core includes a whey protein, a soy protein and/or a pea protein.

In some embodiments, the micronutrient comprises at least one ion selected from the group consisting of iron, cobalt, chromium, copper, iodine, manganese, selenium, zinc, molybdenum, calcium, sodium, chloride, magnesium, potassium, or any of the combination thereof.

In some embodiments, the microparticle further may include minerals, vitamins, fiber, bile acids, probiotics, prebiotics, flavoring agents, coloring agents, excipients, hydrogel, preservatives, and/or any combination thereof.

In some embodiments, the core may be of a spherical shape, an irregular shape, or agglomerated shapes. The microparticle may have a diameter from about 50 µm to about 2000 µm. In some other embodiments, the microparticle has a diameter from about 0.1 mm to about 4 mm.

In some embodiments, the enteric coating comprises one or more of a resistant starch, gelatin, cellulose, modified cellulose, chitin, a GRAS coating, a methacrylic acid copolymer, an alginate, a shellac, a carboxymethylcellulose, EUDRAGUARD® Natural, Nutrateric® Nutritional Enteric Coating System, insoluble fibers, and/or any combination of these polymers with or without other materials.

In some embodiments, the enteric coating is acid-resistant. The enteric coating can further be configured to be dissolved in the upper intestine of an individual. The enteric coating is not substantially dissolved, and the nutrients are not substantially released, at a pH less than about 3.5.

The core and/or the enteric coating in accordance with the present disclosure may include one, two or more layers. The thickness of the enteric coating may be non-uniform.

In some embodiments, the enteric coating dissolves at a pH above about 6.5.

The present disclosure also provides a composition including a microparticle in accordance with the present disclosure, and a carrier. The carrier may be solid, semi-solid, or liquid. In some embodiments, the carrier has a pH between about 2.5 to about 3.5. In some other embodiments, the carrier has a pH below 5. In some embodiments, the carrier includes at least one of minerals, vitamins, fiber, bile acids, probiotics, prebiotics, flavoring agents, coloring agents, excipients, hydrogel, preservatives, and/or any combination thereof.

In some embodiments, the carrier is in a liquid form, and is configured to be administered together with the microparticle for oral ingestion.

Methods of using the microparticles and compositions are also provided to deliver nutrients directed to the upper intestine, by administering to the upper intestine an effective amount of the microparticle or composition in accordance with the present disclosure.

In some embodiments, an effective amount, about 25 kcal to 1000 kcal per dose, of the microparticle or composition is administered in accordance with the present disclosure. The effective amount may be administered from about once to about 12 times per day, or an ad lib or as desired basis.

In some embodiments, the effective amount of the microparticle or composition is released at a pH about 6.5 or above.

The method may further be used in conjunction with weight loss or blood glucose control strategies such as anti-diabetic and weight loss medications or devices such as gastric band, intragastric balloon, or intestinal sleeve.

The method may further include measuring a glucose level, and adjusting the effective amount to the individual based on the measured glucose level.

Further provided are methods for treating an individual for a condition, e.g., treating type 1 diabetes, treating type 2 diabetes, treating pre-diabetes, preventing diabetes mellitus, preventing recurrence of diabetes mellitus, maintaining diabetes in remission, promoting weight loss, maintaining weight, and controlling appetite and also preventing and treating obesity related co-morbidities. In some embodiments, the method includes selecting the microparticle and the carrier as disclosed in the present disclosure, administering an effective amount of the microparticle by oral ingestion by a patient, and administering the carrier by oral ingestion by the patient. In some embodiments, a beverage is created by mixing the microparticle and carrier together, prior to administration. The effective amount can be administered about one to 12 times a day, or taken ad lib.

The present disclosure also provides a matrix embedded composition comprising at least one macronutrient and optionally one or more micronutrients, excipients, hydrogels, bile acids, probiotics, and/or preservatives, wherein the matrix comprises one or more succinylated protein. The matrix is configured to be dissolved, and the nutrients are configured to be released, in the upper intestine, and/or at a pH about 6.5 and/or above. The embedded composition or nutrients are not configured to be substantially released, and the matrix is not configured to be dissolved, at a pH less than about 3.5. In some embodiments, the succinylated protein comprises succinylated gelatin or succinylated β-lactoglobulin.

Also provided is a method for treating an individual for a condition selected from the group consisting of: treating type 1 diabetes, treating type 2 diabetes, treating pre-diabetes, preventing diabetes mellitus, preventing recurrence of diabetes mellitus, maintaining diabetes in remission, preventing, treating and maintaining in remission comorbidities relating to excess fat mass, managing glucose control, minimizing glucose variability, promoting weight loss, maintaining weight, and controlling appetite, and preventing and treating obesity related co-morbidities, the method comprising selecting at least one macronutrient comprising at least one succinylated protein; and administering to a upper intestine of the individual an effective amount of the at least one macronutrient.

DETAILED DESCRIPTION

Figure 1:
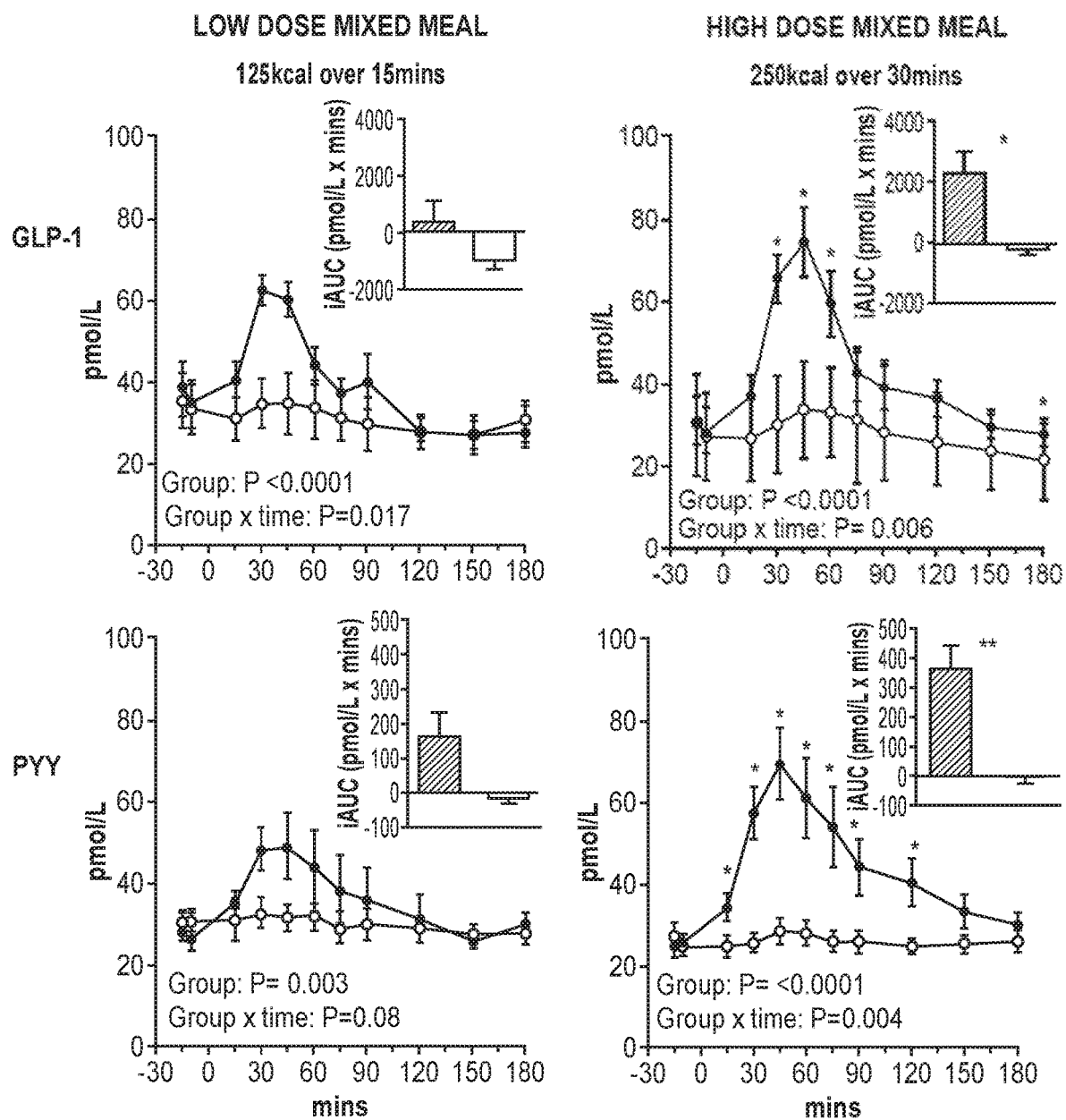
FIG. 1 shows the hormone response in a proof-of-concept human tube-feeding study.

Throughout this application, the text refers to various embodiments of nutrients, physical compositions, methods, devices, and systems. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

Also throughout this disclosure, various publications, patents, and published patent specifications are referenced by an identifying citation. The disclosures of these publications, patents and published patent specifications are hereby incorporated by reference into the present disclosure to more fully describe the state of the art to which this invention pertains.

Definitions

The singular forms "a", "an," and "the" include plural references unless the context clearly dictates otherwise. For example, the term "a nutrient" includes a plurality of nutrients, including mixtures thereof.

Numerical designations and numerical ranges, for example pH, temperature, time, concentration, and molecular weight, are approximations which are varied (+) or (−) by increments of 0.1. It is to be understood, although not always explicitly stated, that all numerical designations are preceded by the term "about". It also is to be understood, although not always explicitly stated, that the reagents described herein are merely exemplary and that equivalents of such are known in the art.

The term "comprising" intends that formulations, physical compositions and methods include the recited elements but do not exclude others. "Consisting essentially of" when used to define formulations, physical compositions, and methods, shall mean excluding other elements of any essential significance to the combination such as those that do not contribute to the therapeutic benefit of the claimed embodiments. Thus, a physical composition consisting essentially of the elements as defined herein would not exclude trace contaminants from the isolation and purification method and pharmaceutically acceptable carriers, such as phosphate buffered saline, preservatives, and the like. "Consisting of," shall mean excluding more than trace elements of other ingredients. Embodiments defined by each of these transition terms are within the scope of this invention. In one aspect, the composition consists essentially of absorbable metabolizeable macronutrients and excludes non-metabolized and non-absorbed agents, e.g., artificial sugars such as sucralose and equivalents thereof.

The term "subject" intends an animal, whether human or non-human. For example, an individual may be human, bovine, horse, feline, canine, rodent, or primate.

The term "effective amount" intends an amount sufficient to effect beneficial or desired results. An effective amount may be administered in one or more administrations, applications, or dosages. Such delivery is dependent on a number of variables including the time period for which the individual dosage unit is to be used, the bioavailability of the content of the microcapsule if administered in a microcapsule, the route of administration, etc. It is understood, however, that specific dose levels including the contents of the microcapsule of the present disclosure for any particular subject depends upon a variety of factors, including the activity of the specific compound employed, bioavailability of the contents of the microcapsule, the route of administration, the time of administration, the rate of excretion, the contents of the microcapsule, the severity of the particular disorder being treated, the form of administration, and the individual's age, body weight, general health, sex, and diet. Treatment dosages generally may be titrated to optimize safety and efficacy and to minimize side-effects.

The term "treating" or "treatment" of a condition or disease intends (1) preventing the symptoms or condition from occurring in an individual (human or animal) that is predisposed or does not yet display symptoms of the disease, (2) inhibiting the disease or arresting its development, (3) ameliorating or causing or maintaining regression of the disease or the symptoms of the disease, (4) or managing a disease or condition. For example, "treating" or "treatment" of a condition or disease includes, but is not limited to, symptom alleviation or amelioration, management of the disease or condition or symptoms of the disease or condition, diminishment of an extent, stabilization (i.e., not worsening), delay or slowing of progression, amelioration or palliation, and remission (partial or total), whether detectable or undetectable. One can determine if treatment has been successful by noting clinical or subclinical symptoms. For example, one can test for the blood glucose level after administration of the composition.

The term "macronutrient" intends lipid, fat, oil, carbohydrate or protein and includes both simple and complex versions of these alternatively termed digested or elemental versions and undigested versions.

The term "micronutrient" intends nutrients required by humans and other living things throughout life in small quantities. Non-limiting examples of micronutrients include iron, cobalt, chromium, copper, iodine, manganese, selenium, zinc, molybdenum, vitamins, calcium, sodium, chloride, magnesium, and potassium. The following reference lists of micronutrients are also incorporated herein by reference:
wikipedia.org/wiki/List_of_micronutrients;
wikipedia.org/wiki/List_of_phytochemicals_in_food.

The term "nutrient" intends a macronutrient, a micronutrient, or both.

The term "microparticle" intends without limitation nanoparticles, microspheres, nanospheres, microcapsules, nanocapsules, and particles, in general. As used herein, the term microparticle refers to coated or encapsulated nanoparticles, microspheres, nanospheres, microcapsules, nanocapsules, and particles including a core and a coating. The term "microparticle" refers generally to particles that have diameters in the range of about 10 nanometers (nm) to about 4 mm (millimeters), or alternatively from about 10 nm to about 2 mm, or alternatively less than 2 mm.

The term "contents of the microcapsule" intends without limitation a composition to provide a nutritional benefit, e.g., one or more of macronutrients, micronutrients, proteins, fats, carbohydrates, sugars, amino acids, fatty acids glycerin, alanine, arginine, asparagines, aspartic acid, cysteine, glutamine, glutamic acid, glycine, histidine, isoleucine, leucine, lysine, methionine, phenylalanine, proline, serine, threonine, tryptophan, tyrosine, valine, medium-chain fatty acids (MCFA) with aliphatic tails of 6-12 carbons, and long-chain fatty acids (LCFA) with aliphatic tails longer than 12 carbons, including oleic acid.

The term "sugar" intends such as monosaccharides (e.g., glucose and fructose), disaccharides (e.g., sucrose and lactose), oligosaccharides, and polysaccharides (e.g., starch, glycogen, and cellulose). In one aspect, the term excludes non-nutritive sweeteners, e.g., sucralose and equivalents thereof.

The terms "obese," "non-obese," overweight, and excess weight intend industry-standard definitions. The intention is to specify individuals with excess weight whose weight loss may be expected to have health benefits. For example, an adult obesity standard may include as obese an adult having a body mass index (BMI) of greater than 30 kilogram/square meter (kg/m2). For another example, an adult individual with central obesity but not overall obesity may be categorized as non-obese, where central obesity may be indicated by a waist circumference greater than 102 centimeter (cm) for men and 88 cm for women. Different cultures may define obesity or central obesity differently. A non-obese pediatric individual (between 2 and including 19 years old) may include an individual with BMI less than or equal to the 95th percentile for children of the same age and sex. Relevant to the present disclosure, an individual may be overweight or obese and not meet eligibility standards for bariatric surgery. By way of example, Allergan™'s eligibility requirements for bariatric surgery in 2011 were 30 kg/m2 to 40 kg/m2 with one or more weight-related comorbidity (e.g., hypertension, dyslipidemia, obstructive sleep apnea). Individuals with a BMI greater than 40 kg/m2 were eligible without comorbidity.

The term "locally administer" intends delivery in an inactive form to a specific site for activation at that specific site. A dose of a delivered substance may contain particles that become active at one site and other particles at another site, for example more distally in the gastrointestinal tract. Activity may occur at the site of initial activation as well as elsewhere, particularly more distally in the gastrointestinal tract. A non-limiting example of local administration includes administration at one or more site(s) in the gastrointestinal (GI) tract. A site in the GI tract may be, for example, the stomach, duodenum, jejunum, ileum, colon, or rectum. Administration may be achieved through, by way of example, a time-controlled release formulation or composition, a pH-sensitive controlled-release formulation or composition, or oral ingestion. Administration may be continuous with sustained concentration, continuous with varying concentration, intermittent with sustained concentration, or intermittent with varying concentration. More than one method may be used over the course of treatment. More than one formulation may be administered over the course of treatment. In some embodiments, delivery may be regulated manually. Delivery may be guided by a computing system including, for example, an "app" used by the patients or the physicians.

A "composition" typically intends a combination of the active agent, e.g., compound or composition, and a naturally-occurring or non-naturally-occurring carrier, inert (for example, a water, detectable agent or label) or active, such as an adjuvant, diluent, binder, stabilizer, buffers, salts, lipophilic solvents, preservative, adjuvant, or the like and includes pharmaceutically acceptable or GRAS carriers. A pharmaceutically or nutraceutical or dietary supplement or GRAS acceptable carrier intends one that is suitable for in vivo use, e.g., phosphate buffered saline, water, and the like.

In a further aspect, the composition further comprises instructions for use to the patient or consumer.

"Upper intestine" refers to the duodenum, the jejunum, and/or the first part of the ileum.

As used herein, the term "kit" intends a combination of elements provided together but not admixed. For example, in one aspect, a kit comprises one or more microparticles and one or more carriers. As described herein, in certain embodiments, the microparticle and the carrier are not administered in the same composition but are provided separately and then combined upon administration, for example, one can orally administer the microparticle and then subsequently administer the carrier. Alternatively the carrier is administered first and the microparticle is subsequently administered. In a yet further aspect, the microparticle and the carrier are mixed just prior to use and administered together. In a further aspect, the kit further comprises instructions for use.

Use of the Compositions and Methods

The compositions and methods in accordance with the present disclosure work to simulate some or all of the features of the delivery of nutrients directly to the upper intestine that occurs after gastric bypass. The compositions and methods in accordance with the present disclosure also work to simulate some or all of the features of the delivery of nutrients that occur after the sleeve gastrectomy procedure, in particular, more rapid appearance of digested and undigested nutrient in the upper intestine than occurs in the normal un-operated state.

Nutrient delivery following gastric bypass is characterized by rapid appearance of simple and complex macronutrients in the mid jejunum. Some nutrients are metabolically active at the site of delivery and some pass more distally to the mid-distal jejunum or the illeum, before they are digested and absorbed. This altered pattern of nutrient delivery following gastric bypass is considered to trigger some or all of the multiple metabolic pathways that control appetite and blood glucose by direct local and/or indirect actions elsewhere in the body, including more distally in the gastrointestinal tract. The triggered pathways may lead to rapid clinical improvement benefits (e.g., enhanced release of endogenous insulin or delayed improvement, e.g., weight loss due to prolonged appetite suppression and caloric restriction). Pathways activated may include hormonal modulation, altered neural and neurohormonal signaling, altered bile acid, altered gut microbiome, altered osmotic load and pressure in the intestine, avoidance of triggering of release of anti-incretin from the stomach and upper intestine. (Abdeen G. et. al. (2015) Obes Surg.; Bojsen-Moller, K. N. (2015) Dan Med J. 61(4); Habegger, K. M. et al. (2014) Gut. 63(8):1238-1246; Kaplan, L. (2012) Myths Associated with Obesity and Bariatric Surgery—Myth 2: "Bariatric surgery induces weight loss primarily by mechanical restriction and nutrient malabsorption," available at bariatrictimes.com/myths-associated-with-obesity-and-bariatricsurgery %E2%80%94myth-2-% E2%80%9Cbariatric-surgery-inducesweight-loss-primarily-by-mechanical-restriction-and-nutrientmalabsorption-% E2%80%9%; Knop, F. K. et al. (2013) Diabetes Care 36(Suppl 2):S287-S291; Lutz, T. A. et al. (2014) Dig Surg. 31(1):13-24; Maffei, A. et al. (2015) Mol Endocrinol. 29(4):542-557). Although the anatomical changes, nutrient and foregut secretion rerouting, and the clinical benefits of gastric bypass are well documented, the mechanism behind such clinical benefits are still being investigated. The compositions and methods described herein may achieve the aforementioned benefits by a mechanism or mechanisms not yet identified. Following sleeve gastrectomy, some of the same nutrient delivery mechanisms occur as after gastric bypass and some of the same actions.

In accordance with some embodiments, the compositions and methods also minimize problems associated with gastric bypass surgery and related surgical procedures. As the amounts and types of nutrients interacting with the gastrointestinal tract may be modified by selecting a desired formulation, normal absorption of micronutrients in the upper gastrointestinal tract may be achieved. Further, the non-surgical and non-invasive approach avoids the costs and risks of surgery. In addition to simulating pathways activated by gastric bypass and related surgical procedures, the composition and methods in accordance with some embodiments also activate beneficial gut-based metabolic pathways not otherwise available with gastric bypass and related surgical procedures. For one example, the ileal brake, a distal ileal feedback mechanism, may be activated, increasing satiety and reducing food intake. (van Avesaat, M. et al. (2015) Int J Obes (Lond) 39(2):235-243.) For another example, optimal dietary fiber intake may be achieved. (Dahl, W. J. et al. (2015) J Acad Nutr Diet. 115(11):1861-1870). The benefits of the composition and methods in accordance with some embodiments further include, but are not limited to, avoidance of irreversible surgical changes and the option of variables, including intermittent or a cessation of stimulation of pathways to minimize tolerance and adverse effects.

The nutrient-based therapeutic platform in accordance with the present disclosure leads to the sudden appearance of macronutrients, and optionally micronutrients, in the upper intestine. In accordance with the present disclosure, the rate of appearance of nutrients in the upper intestine is more rapid than that following ordinary food ingestion, thereby simulating the rapid delivery of nutrients to the upper intestine that occurs following gastric bypass and related surgical procedures. Nutrient interaction with the intestine and hence metabolic activity may occur not just at one site but at several sites, depending on the uncoating of the nutrients, the state of digestion and access to and interaction with intestinal receptors. In some embodiments, the nutrient-based therapeutic platform simulates nutrient action at multiple gastrointestinal levels. The macronutrients in accordance with some embodiments experience minimal interaction with the upper gastrointestinal tract, namely, the stomach, duodenum, and proximal jejunum, its secretions or excretions, thereby simulating gastric bypass and related surgeries and possibly preventing the release of factors that promote poor glucose tolerance, e.g., the anti-incretins and other undesirable factors. (Mingrone, G. et al. (2014) Nat Rev Endocrinol. 10(2):73-74; Kamvissi, V. et al. (2015) Horm Metab Res. 47(1):84-87). In accordance with some embodiments, the platform allows for the compositions and methods to be adjusted to meet individual and specific needs.

Mechanisms behind the benefit of rapid appearance of nutrients in the upper intestine are still under investigation, which include, but are not limited to, mechanisms disclosed in Batterham, R. L. et al. (2016) Diabetes Care 39(6):893-901, which is incorporated herein by reference in its entirety. Pathways directly simulated in accordance with the current disclosure include, but are not limited to, those listed under heading "Immediate Impact of Surgery" especially caloric restriction induced by appetite suppression, rapid emptying of nutrients into the small intestine, exclusion of the duodenum and proximal jejunum form nutrients, and enhanced nutrient/bile delivery to the mid/distal jejunum and ileum. By activating these pathways, the potential mediators and mechanisms of gastric bypass are activated leading to beneficial effects on glucose homeostasis. In addition to effects on glucose, similar pathways lead to appetite suppression, alteration in taste preference, reduced caloric intake, increased energy expenditure and over time weight loss, as well as improvement in obesity and associated co-morbidities. Activation of mechanisms directly in response to nutrients may lead to activation of secondary and tertiary mechanisms that have effects over a more prolonged period than the primary pathway.

The compositions and methods are useful to control weight and blood glucose, manage hunger, and regulate satiety and appetite and alter taste preferences by administering an effective amount of the compositions to a subject in need thereof.

Thus, in one aspect, the compositions and methods are useful to manage, treat, or prevent obesity, diabetes mellitus, type 2 diabetes, type 1 diabetes, and related disorders and co-morbidities as well as to treat or prevent pre-diabetes, recurrence of diabetes mellitus, and maintaining diabetes in remission. Individuals with Type 1 diabetes may benefit from use of the platform such as weight loss through enhanced satiety and reduced caloric intake and/or through activation of the ileal brake to slow gastric emptying.

Also provided are methods for use of the microparticles for the delivery of nutrients to an individual. The compositions and uses thereof will vary depending on the mode of the use of the compositions.

The nutrient-based therapeutic platform in accordance with the disclosure can be practiced through a variety of delivery methods. In some embodiments, delivery of the nutrients is achieved through a delivery device, such as an enteral feeding tube described in U.S. Provisional Patent Application No. 62/182,361, filed Jun. 19, 2015, which is incorporated herein by reference in its entirety. In some embodiments, the nutrients are coated in an enteric coating or delayed release coating and desired release profile is achieved by the selection of the coating or matrix, and the core. A carrier can also facilitate achieving the desired release profile by delivering the microparticle or matrix to a specific site in the gastrointestinal tract. In some embodiments, the nutrients are embedded in a matrix which protects the nutrients from digestion and absorption in the stomach such as described by Cailard et al., using Biovelia products. See, http://biovelia.com/node/26, Poulin, J. F. et al. (2011) Int J Pharm. 405(1-2):47-55, which are incorporated herein by reference in their entirety.

In yet some other embodiments, the nutrients are modified to resist digestion in the stomach while allowing for digestion and absorption in the upper intestine. A non-limiting example of such embodiments is modified protein such as succinylated gelatin, succinylated β-lactoglobulin, and modified proteins described in www.old.health.gov.il/units/pharmacy/trufot/alonim/3343.pdf and Caillard, R. et al. (2012) Int J Pharm. 437(1-2):130-136, which are incorporated by reference herein in their entirety.

In some embodiments, a storage depot or a reservoir is configured to release the nutrients at a selected rate and site. In yet some other embodiments, prokinetic agents are added to the nutrients to accelerate delivery in the upper intestine.

As will be appreciated by a person skilled in the art, delivery methods in accordance with the disclosure are not limited to the above described embodiments and may include any other known methods that allow for delayed release of the nutrients and/or devices that direct deliver nutrients to the upper intestine. It should also be understood that the above described embodiments may be combined to meet the individual and specific needs.

In some embodiments, GRAS coatings and self-asserted GRAS coatings are used. Non-limiting examples of such GRAS coatings include pH sensitive GRAS enteric coatings such as Colorcon's Nutrateric™ (Ethylcellulose and Sodium alginate) and Sensient Pharma's Protect™ Enteric (Aqueous Shellac and Alginate), time and pH sensitive GRAS enteric coatings such as Evonik's Eudraguard Natural™ (Starch Acetate), and whey-alginate coating and casein-alginate coatings. The coating materials can be caloric, non-caloric, and may itself be a nutrient or providing health benefit. As a non-limiting example, succinylated gelatin resists digestion in the stomach, but is digested by intestinal enzymes in more neutral or alkaline pH in the intestine. Coatings may comprise dietary fiber and provide the therapeutic benefit of dietary fiber.

In accordance with some embodiments, modified compositions and formulations are modified to accelerate gastric emptying for achieving optimal digestion. Studies have shown that food structure and texture affect stomach emptying, and the addition of acid-instable emulsions to preprocessed foods lead to accelerated gastric emptying, which may provide benefits to patients with diabetes mellitus by increasing satiety and suppressing food intake. (Kong, F.S.R.P. (2008) Journal of Food Science 73(5):R67-R80.) Therefore, the compositions and formulations may be modified accordingly to control the rate of release of macronutrients and to reduce or increase the rate of stomach emptying.

In accordance with some embodiments, nutrients are delivered using the delivery system described by Biovelia which provides gastro-protection of encapsulated nutraceutical and pharmaceutical products.

Microparticles

One aspect of the present disclosure provides compositions comprising, or alternatively consisting essentially of, or yet further consists of, a macronutrient, and optionally a micronutrient, core encapsulated in an enteric coating. The coating shields the core from digestion until the microparticle reaches the upper intestine, wherein the coating is dissolved in the neutral or alkaline intestinal environment, for example, at a pH about 6.5 and/or above. The coating material delivers the nutrient-filled core in an inert, stabilized state to the upper intestine where it is released, i.e., where the compounds are destabilized, digested and absorbed. The coating may comprise, or alternatively consist essentially of, or yet further consist of multiple components that alone or in combination manage the release of the nutrients.

Other components may also be added to the core, coating or both. Non-limiting examples of such other components include excipients, minerals and vitamins, fiber, hydrogels, bile acids, flavoring agents, coloring agents, and preservatives. The core may have a spherical shape, an irregular shape, or agglomerated shapes.

The caloric load for each dosage of the compositions in accordance with some embodiments may be in ranges of, for example, about 0-50 calories, about 50-100 calories, about 100 to 150 calories, about 150 to 200 calories, about 100 to 200 calories, about 200 to 250 calories, about 250 to 300 calories, about 300 to 350 calories, about 350 to 400 calories, about 400 to 450 calories, and about 450 to 500 calories. The calories load per dosage preferably is larger than that may be contained in a standard capsule form.

In some embodiments, the nutrients are contained in microparticles having a diameter of less than 2 mm, for example, from about 0.1 mm to about 0.3 mm, from about 0.3 mm to about 0.5 mm, from about 0.5 mm to about 0.6 mm, from about 0.6 mm to about 0.7 mm, from about 0.7 mm to about 0.8 mm, from about 0.8 mm to about 0.9 mm, from about 0.9 mm to about 1.0 mm, from about 1.0 mm to about 1.1 mm, from about 1.1 mm to about 1.2 mm, from about 1.2 mm to about 1.3 mm, from about 1.3 mm to about 1.4 mm, from about 1.4 mm to about 1.5 mm, from about 1.5 mm to about 1.7 mm, and from about 1.7 mm to about 2.0 mm. In some embodiments, a carrier vehicle is selected to maintain the microparticles in an inert state until being released in the upper intestine. In some embodiments, the carrier vehicle is a liquid configured to administer the compositions as a beverage, such that the full dose may be easily ingested without chewing. In some other embodiments, the carrier is a semisolid or solid form.

The microencapsulation of the nutrients in accordance with one aspect of this disclosure allows an adequate nutrient stimulus (stimuli) to be delivered directly to the upper intestine in a formulation that is easy to ingest. Without being bound by theory, Applicant believes that this method allows for simulation of rapid delivery and/or appearance of nutrients to the upper intestine that occurs following gastric bypass. This rapid delivery of nutrient triggers multiple synergistic salutary metabolic pathways that control appetite and blood glucose, including, but are not limited to, activating the release of GLP-1, PYY, insulin, and other gluco-regulating and/or appetite regulating factors.

In one aspect, the encapsulated microparticles are suspended in a compatible carrier medium or solution to allow for easy ingestion and rapid transport to and release in the upper intestine. Thus in one aspect, the disclosure also provides compositions comprising a macronutrient microparticle and a carrier, such as a compatible carrier or solution to allow delivery to the intestines upon ingestion. The carriers can be solid, semi-solid, or liquid. The carrier in accordance with the present disclosure preferably is a non-caloric or low-caloric liquid that suspends the microparticles and preserves the integrity of the coating. Non-limiting examples of the carrier include Schweppes Diet Tonic Water for use with pH sensitive coatings, or other "diet" drinks of low pH. To facilitate ingestion of microparticles, a solid or semi-solid binder can be used. Such binder preferably is a non-caloric or low-caloric liquid that preserves the integrity of the coating. Non-limiting examples of such carriers are disclosed herein and known in the art.

Normally, liquids with a calorie density of 1 kcal/mL are emptied at about 2 to 2.5 mL/min, whereas liquids of 0.2 kcal/mL are emptied at about 10 mL/min. (Kong, F.S.R.P. (2008) Journal of Food Science 73(5):R67-R80). By shielding the caloric load partly or completely from digestion, and mucosal interaction and absorption in the stomach and upper intestine, preferably up to at least the mid jejunum, the rate of emptying of the microparticles in accordance with the present disclosure will be faster than without an enteric coating, in the range of approximately 4 kcal/min to approximately 20 kcal/min in the upper intestine. The signal to slow gastric emptying derives from the appearance of nutrients in the upper intestine. Active nutrients in accordance with the present disclosure only appear after the effective dose has been emptied from the stomach, and does not prevent or unduly delay gastric emptying. In some embodiments, the effective dose is approximately 80% to-100% of the orally ingested dose.

Matrix

In accordance with some embodiments, macronutrients are embedded in a matrix material, thereby shielding the macronutrients from acid digestion. The matrix material in accordance with the present disclosure includes, but is not limited to, succinylated gelatin that resists acid digestion in acidic pH typical of that found in the stomach but is digestible in more alkaline pH such as found in the upper intestine in the presence of digestive enzymes. During succinylation, a succinyl group ($-CO-CH_2-CH_2-CO-$) is added to a lysine residue of a protein molecule. Succinylation changes lysine's charge from +1 to −1 and introduces a relatively large structural moiety that leads to significant changes in protein structure and function. Such protein modification may be naturally occurring, and may be found in many proteins, including histones.

The components embedded in the matrix, for example, a macronutrient and optionally a micronutrient, may be selected from the components described below.

Components

The microparticle in accordance with the present disclosure includes a core comprising one or more types of absorbable macronutrient, including protein, carbohydrate, and/or fat. These components may be in a variety of proportions to optimize certain desired characteristics, e.g., a higher proportion of carbohydrate may be included to increase satiation whereas a lower amount may be used for greater glucose control. These components may be in different amounts. Macronutrients may be in elemental or more typically in complex forms.

Proteins may be in the form of amino acids, peptides, or proteins, and may be of animal or plant origin. Carbohydrates may be in the form of monosaccharides, disaccharides or polysaccharides and may be of animal or plant origin, including lactose. Lipids, fats and oils may include saturated and/or unsaturated and/or monounsaturated fatty acids, and may include fatty acids having long, medium, and short chain length, and may be of animal or plant origin.

"Ensure® Original" Nutrition Shake, sugar spheres, and whole milk power have been used in Applicant's preclinical studies and the same or similar macronutrient ingredients are considered appropriate ingredients for one embodiment of the current invention's core.

Non-limiting examples of a macronutrient core are listed in Table 1 below.

TABLE 1

| CORE | | | | | |
|---|---|---|---|---|---|
| Macronutrient | Diameter | Shape | Mfring | Layers | Links |
| Whole Milk Powder (WMP) + sucrose | Sucrose 0.2 mm | Spherical | Spray coat reconstituted WMP on sucrose starter seed | 2: sucrose center; WMP outer layer | example https://www.fonterra.com/ au/en/NZMP+Ingredients/ Our+Ingredients/ Milk+Powders/ Whole+Milk+Powder |

TABLE 1-continued

| CORE | | | | | |
|---|---|---|---|---|---|
| Macronutrient | Diameter | Shape | Mfring | Layers | Links |
| Sucrose | 1 mm | Spherical | Prefabricated | 1 | example http://www.colorcon.com/ products- formulation/all- products/excipients/ multiparticulates/suglets |
| Non instantized Whey Protein Isolate (WPI) + Sucrose | Sucrose 0.2 mm | Spherical | Spray coat reconstituted WPI on sucrose starter seed | 2: sucrose center; WP outer layer | example https://www.fonterra.com/ global/en/our+products/ our+ingredients/ products/whey+protein+ concentrates+and+isolates |
| Mixed Meal(MM) + sucrose ratio protein:CHO:fat aapprox 2:1:1 and 1:2:1 | Sucrose 0.2 mm | Spherical | Spray coat reconstituted WPI or pea or soy protein(VP) and then lecithin on sucrose starter seed | 3: sucrose center; WPI or VP mid layer Lecithin outer layer | example http://www.cargillfoods. com/na/en/products/ lecithin/ |
| Vegetable Protein: Pea protein or alternatively Soy Protein (VP) + sucrose | Sucrose 0.2 mm | Spherical | Spray coat reconstituted VP on sucrose starter seed | 2: sucrose center; VP outer layer | example http://www.pea- protein.com/ |
| Ensure Nutrition (ENP) Powder + sucrose | Sucrose 0.2 mm | Spherical | Spray coat reconstituted ENP on sucrose starter seed | 2: sucrose center; ENP outer layer | https://ensure.com/nutrition- products/ensure-powder?utm_ source=google&utm_medium= cpc&utm_term= ensure%20powder&utm_ content=ensure%20powder_ exact&utm_campaign=brand_ brand%20recognition_exact |

Pre-manufactured macronutrient particles may also be used, e.g., sucrose non-pareil microparticles. Non-limiting examples of such are described in Douaire and Norton (2013) J. Sci Food Agric. 93:3147-3154 and Nedovic et al. (2011) Procedia Food Science 1:1806-1815.

In addition to a macronutrient core and a protective coating, other components may be part of the system to optimize effect and increase acceptability and value. Optional components of the core in accordance with the present disclosure include micronutrients and non-nutrient components. Additional components may include: micronutrients, minerals and electrolytes, fiber, preservatives, coloring, flavoring, osmotically active components, bile salts, probiotics, prebiotics, excipients, and components for increasing pressure in the intestine, e.g., hydrogel incorporated in a manner to be released at the desired site and/or bile acids shown to activate metabolic pathways associated with metabolic control following sleeve gastrectomy and other bariatric surgical procedures.

The proportions of nutrients in the core can be adjusted as desired for different health goals e.g. a low carbohydrate formulation may be preferred for patients with high blood glucose.

Form

The core is in a microparticulate form which may be granules, spheres, or agglomerated shapes. These may be commercially available or prepared specifically for the product. The form of Nutracept preferably is suitable for encapsulation. A spherical shape may help minimize the amount of coating material needed.

Coating

The coating allows nutrients to be delivered in a manner that simulates aspects of gastric bypass including: exclusion of nutrient contact with the upper gastrointestinal tract mucosa (mouth, esophagus, stomach, and preferably part of small intestine especially the duodenum and first half of the jejunum but may extend further including up to the mid small intestine); rapid exposure of the upper and especially mid-small intestine to macronutrient with local and/or more distal gastrointestinal and systemic actions.

The mode of action of the coating may be pH and/or time-dependent. In one embodiment, the coating comprises a delayed release coating. In another embodiment, the coating comprises an enteric coating. The coating is configured to shield the core in pH less than approximately 3.5, such that the core is not substantially dissolved in an acidic environment. In some embodiments, approximately 80% of the nutrient core will be retained in gastric pH for about two hours. The coating further is configured to uncoat at pH over approximately 6. In some embodiments, approximately 80% of remaining nutrients in the core are released in the upper intestine within three hours. The release of nutrients in accordance with the present disclosure occurs in a manner that does not feedback to unduly slow release of ingested nutrient form the stomach. Acid resistant coatings that are pH sensitive and time-sensitive, e.g., Colorcon's Nutrateric and Evonik's Eudraguard Natural, may be used to achieve the appearance of approximately 80% to approximately 100% of nutrients in the upper intestine prior to uncoating.

The coating may comprise a GRAS material or a metabolically inert (i.e. non-digestible) and safe material when orally ingested in the desired amount within the Acceptable Daily Intake. The enteric coating comprises different polymers and combinations thereof, e.g. resistant starches, other insoluble fibers, etc. Non-limiting examples of enteric polymers include: (1) cellulose including semisynthetic cellulose, e.g. ethyl cellulose, methacrylic acid copolymer, alginate, shellac, carboxymethylcellulose; (2) resistant starch including semi-synthetic starches, e.g., starch acetate, insoluble fibers, and/or (3) any combination of these polymers with or without other materials.

Different components may be used in different ratios in the coating to achieve the desired characteristics. For example, alginate may be used as "pore former" to increase the porosity of the microparticle. In addition, general cellulose and other dietary fibers, e.g., starch acetate, are preferably applied at a coating level of less than 20% where possible to yield a daily intake of fiber approximating the recommended daily intake of 25 g/d for women and 38 g/d for men, although higher levels are permissible if well tolerated.

In some embodiments, the coating material may provide additional nutritional or other health benefit, and may be digestible or non-digestible. If non-digestible, the coating may be metabolically inert or serve a role e.g., as fiber or bulking agent in the gut or aid in glucose and/or cholesterol lowering and/or provide other heath attributes described for dietary fiber including increasing GLP-1 and other glucose and appetite regulating hormones.

The coating may comprise one or more layers of coating of one or more materials.

Exemplary cores listed in Table 1 can be spray coated with Eudraguard Natural or Nutrateric to obtain microparticles having a diameter in the range of about 1.5 mm to about 2.0 mm. The coating loading preferably is less than 20% by weight, such that total daily dose is within ADI and well tolerated. The release of the above mentioned coating is characterized by minimal release (e.g., less than 20%) at pH 1.2 for 2 hours and full release (e.g., at least 80%) at pH 6.5 over 3 hours.

Size

The microparticles in accordance with the present disclosure may generally have a diameter from approximately 0.5 mm to approximately 2.0 mm, and are preferably in the size range of about 50 µm to 1000 µm or alternatively from about 50 µm to 750 µm, or alternatively from about 50 µm to 500 µm, or alternatively from 75 µm to 1000 µm, or alternatively from about 75 µm to 750 µm, or alternatively from about 75 µm to 500 µm, or alternatively from 100 µm to 1000 µm, or alternatively from 100 µm to 750 µm, or alternatively from about 100 to about 500 µm, or alternatively from about 200 µm to about 400 µm.

The smallest possible particle size is preferably selected consistent with effective coating to facilitate ingestion and tolerability.

Manufacturing Process

Macronutrients, either together or individually, are processed into microparticle cores by high shear wet granulation, spray drying, or extrusion spheronization, methods as described in Mei et al. (2104) Applied Materials & Interfaces 6:5962-5970 and Douaire and Norton (2013) J. Sci Food Agric. 93:3147-3154, or any other method known in the art. The core may comprise a seed of macronutrient or other material inside the core to which macronutrient and other core components are added. The core may comprise different layers, which may be applied using different techniques. For example, a core may start with a starter seed formed through extrusion spheronization or agglomeration, and several different layers may then be spray coated over starter seed. Different components of the nutrient core may be coated in different layers or, alternatively, mixed to form a core.

Alternate microparticle manufacturing techniques include, without limitation: other wet granulation processes (e.g., fluid bed); spray layering of macronutrient solution, suspension, and/or emulsion onto seed cores via Wurster fluid bed coating or other coating techniques; dry granulation (e.g., roller compaction).

The core may comprise a structured multilayer or a matrix arrangement, or an irregular structure.

The coating may be formulated to modify release characteristics. For example, alginate that forms pores in a capsule with a neutral pH may be adjusted to increase the size of the pores. For another example, the thickness of a starch acetate coating may be increased to delay uncoating of the core.

Methods for encapsulating the core comprise precipitates, spray drying, spray coating, fluidized bed coating, high shear wet or dry granulation, agglomeration, extrusion spheronization, methods described in Nedovic et al. (2011) Procedia Food Science 1:1806-1815, or any other method known in the art.

In another aspect, the macronutrients can be wet or dry granulated with the enteric polymers, spray dried with a solution, suspension, and or emulsion of macronutrients in a solution of enteric polymer, or utilizing micro emulsification. A variety of techniques may be used for microencapsulation as described in the literature, including techniques described in Douaire and Norton (2013) J. Sci Food Agric. 93:3147-3154 and Nedovic et al. (2011) Procedia Food Science 1:1806-1815 and en.wikipedia.org/wiki/Micro-encapsulation, which are incorporated herein by reference in their entirety.

Preferred manufacturing methods are ones that are scaleable, cost effective, yield consistent product and require minimal coating material.

Carrier

In one aspect, the encapsulated microparticles in accordance with the present disclosure are administered with a compatible solid or liquid carrier medium or solution to allow easy ingestion and rapid transport to and release in the upper intestine. The carrier may be formulated, e.g., pH adjusted to maintain nutrient encapsulated until release at desired site. The formulated carrier may have a pH from approximately 2.5 to approximately 3.5, as the coatings are configured to maintain integrity in acid environments only.

Therefore, in one aspect, the disclosure also provides compositions comprising a macronutrient microparticle and a carrier, such as a compatible carrier to allow delivery to the upper intestine.

The carrier may be in a solid, semi-solid, or liquid form. Non-limiting examples of such carriers include neutral pH carriers such as water, and low pH carriers such as diet tonic water, and any other carrier known in the art. In some embodiments, water serves as a carrier for particles that are released through time sensitive rather than pH sensitive methods.

The specific gravity of the carrier may be similar to the particles, thereby allowing the particles to be suspended in the carrier for easy ingestion and optimal delivery to the upper intestine The carrier may also comprise additional substances to optimize effect and increase acceptability and value. Non-limiting examples include: non-caloric components including micronutrients, minerals and electrolytes, fiber, preservatives, coloring, flavoring, osmotically active components, bile salts, probiotics, prebiotics, excipients, and/or bile acids shown to activate metabolic pathways associated with metabolic control following sleeve gastrectomy and other bariatric surgical procedures.

Substances may be included in the carrier to improve palatability, shelf-life, and stabilization and destabilization of the formulation The microparticles may be mixed with a carrier solution at a time that allows optimal delivery of the nutrient to the desired site. The microparticles may be provided to the consumer in a sachet for mixing just prior to ingestion. The microparticles may be pre-mixed in carrier fluid and ingested as a beverage without further preparation or may be ingested as a soft or firm composition.

In some embodiments, the coated microparticles with cores selected from Table 1 can be administered with a liquid carrier having a pH in the range of about 2.5 to about 3.5. The caloric content of the carrier is preferably between 0 kcal/litre to 10 kcal/litre. One non-limiting example of such carrier is Schweppes Diet Tonic Water, see http://www.schweppesus.com/products/schweppes-diet-tonic-water.

Mode of Use

The microparticles and compositions in accordance with the present disclosure may be administered orally in a manner optimized to meet desired needs (particularly appetite and glucose management). There are many possible ways it may be taken, that include, but are not limited to the following.

The microparticles and compositions may be administered as a monotherapy, in addition to or as a replacement for other therapies, e.g. in addition to a laparoscopic adjustable gastric band, intragastric balloon, or intestinal sleeve, or in place of anti-diabetic or weight loss medication if clinically appropriate.

The microparticles and compositions may be administered from about zero to about 10 or more times per day. Alternatively, an individual may continuously sip the beverage as desired, where the beverage mixed with the microparticles and carriers in accordance with the present disclosure.

In one aspect, the microparticles and compositions may be administered before, during, or between meals, or ad lib to control appetite. The duration of the administration may differ depending on the formulation, e.g., about 1 minute to 20 minutes if in a semi-solid formulation, shorter than 20 minutes if in a beverage formulation, or as desired if administered by frequent sipping.

The dosage of the microparticles and compositions may be fixed, variable based on user characteristics or a certain desired outcome, or as needed to control appetite and aid in blood glucose management The duration of the treatment may be fixed, e.g., one month, or ongoing as needed.

For maximal efficacy and rapid weight loss, the compositions in accordance with the present disclosure may be taken as the sole source of nutrition for short periods of time. For a more moderate effect, the compositions may be taken in the long-term as part of a regular diet.

In some embodiments, the coated microparticles with cores selected from Table 1 can be administered by drinking with the carrier described herein, either premixed as beverage, or separately ingested. In some embodiments, the administration time is preferably less than 5 minutes. A single dose has a caloric load of about 70 kcal to about 250 kcal. In some embodiment, a single dose can have a caloric load of about 150 kcal. The frequency of the administration is 1 to 30 times per day as directed, or as needed to control appetite. In some embodiments, the microparticles are administered 4 times a day, preferably before meal or bedtime, or on empty stomach to aid in appetite control.

There are many advantages of this nutrient-based therapeutic platform. The platform is completely non-invasive, and nutrient based. It may thus be suitable for the majority of individuals worldwide affected by diabetes and obesity and related comorbidities, including the young, the elderly, those with either early or advanced disease, and those of low-income levels.

Unlike many pharmacological agents used for diabetes management (especially sulfonylureas and insulin), there is little risk of side-effects, including hypoglycemia. Clear and measurable outcomes that are expected to be impacted by the nutrient-based therapeutic platform include weight, diabetes control, medication use, cost of medical care and the incidence of other obesity related co-morbidities.

By enhancing the release of appetite-suppressing hormones even in the presence of caloric restriction, the nutrient-based therapeutic platform may enable the body to reset it's body weight "setpoint" to a lower level, allowing for sustained weight loss and less recidivism than occurs with other methods of caloric restriction.

The nutrient-based therapeutic platform further overcomes the problem of providing a nutrient load directly to the intestine in an oral form that is large enough to adequately activate intestinal gluco-regulatory and anorectic (appetite suppressing) pathways. The required nutrient and caloric load, if administered in conventional delayed-release capsules, would require repeated ingestion of approximately 20 or more large capsules four or more times a day, which would be impracticable and unsustainable.

Moreover, unlike gastric bypass, the nutrient-based therapeutic platform permits normal absorption of orally ingested macronutrients and micronutrients as desired. Following gastric bypass, orally ingested calcium and iron bypass the foregut and are poorly absorbed more distally. As the foregut remains fully intact, these substances can be normally absorbed when taken by the usual oral route separately from the nutrient-based therapeutic platform.

An Example of a Microparticle Delivery System: NUTRACEPT™

Nutracept™ is a system that delivers orally ingested microencapsulated macronutrients to the intestine for rapid appearance of nutrients in the upper intestine in order to activate satiety and gluco-regulatory metabolic pathways. The Nutracept™ system is variable by selecting different materials, dosage, intended use, formulation as well as delivery method. The macronutrient core is preferably encapsulated in a GRAS enteric-coated microparticle having a diameter of about 0.5 mm to about 2 mm, which allows the particles to pass through the pylorus without hindrance.

Preferred components of Nutracept™ core include proteins such as animal and/or vegetable protein such as whey protein and pea and soy protein, as well as components that have low allergenicity, components that are well tolerated by patients, as well as those that impose minimal dietary restrictions.

Other components may be added to the macronutrient core. Non-limiting examples of such include, but are not limited to excipients, micronutrients, minerals and vitamins, fiber, hydrogels, bile acids, flavoring, coloring and preservatives and carrier liquids. Non-nutrient components such as super-absorbent hydrogel and fiber promote satiety through non-nutritive pathways such as by mechanical distention. Bile acids are shown to activate metabolic pathways associated with metabolic control following sleeve gastrectomy and other bariatric surgical procedures. (Ryan, K. K. et al. (2014) Nature 509(7499):183-188). Other substances may be included in Nutracept™ to improve palatability, shelf-life, and stabilization, and destabilization of the formulation.

The carrier may also be optimized for palatability and individual needs. Non-nutrient components agents may be included, such as microencapsulated that when released could provide a mechanical satiety signal in the intestine. By making the particles "micro" size and mixed with a carrier liquid, the full dose can be easily ingested without chewing, and the nutrients would be rapidly emptied from the stomach similar to a non-nutrient containing liquid, allowing the nutrients to be delivered in the desired site in the intestine.

The caloric load of Nutracept™ per dose is preferred to be from approximately 25 calories to approximately 1000 calories from one or more macronutrient food groups, with a typical dose between about 75 calories to about 200 calories. The formulation may be in a liquid, semi-solid, or solid form.

The amount of Nutracept ingested can be adjusted to meet medical needs. For maximal efficacy and rapid weight loss, it can be taken as the sole source of nutrition for short periods for example about 1-3 months in duration. For a more moderate effect, it can be taken long-term for examples 3 months to several years with a regular diet.

EXPERIMENTS

Feasibility and optimal formulations of microparticles encapsulating a macronutrient in accordance with the present disclosure may be first evaluated in pre-clinical studies for pH sensitivity and ability to delay release of nutrient absorption, in order to justify human testing.

The following experiments are for illustrative purposes only and should not be interpreted as limitations of the claimed invention. There are a variety of alternative techniques and procedures available to those of skill in the art which would similarly permit one to successfully perform the intended invention. Feeding tube studies were conducted in adults with obesity and type 2 diabetes to establish proof of concept that delivery of uncoated nutrient directly to the upper intestine can induce desired changes in hormones, glucose control and weight with features similar to those seen following gastric bypass.

Experiment No. 1: Targeted Enteral Feeding Simulates Gastric Bypass (the Freedom Study)

Human Tube-Feeding Study

Figure 2:
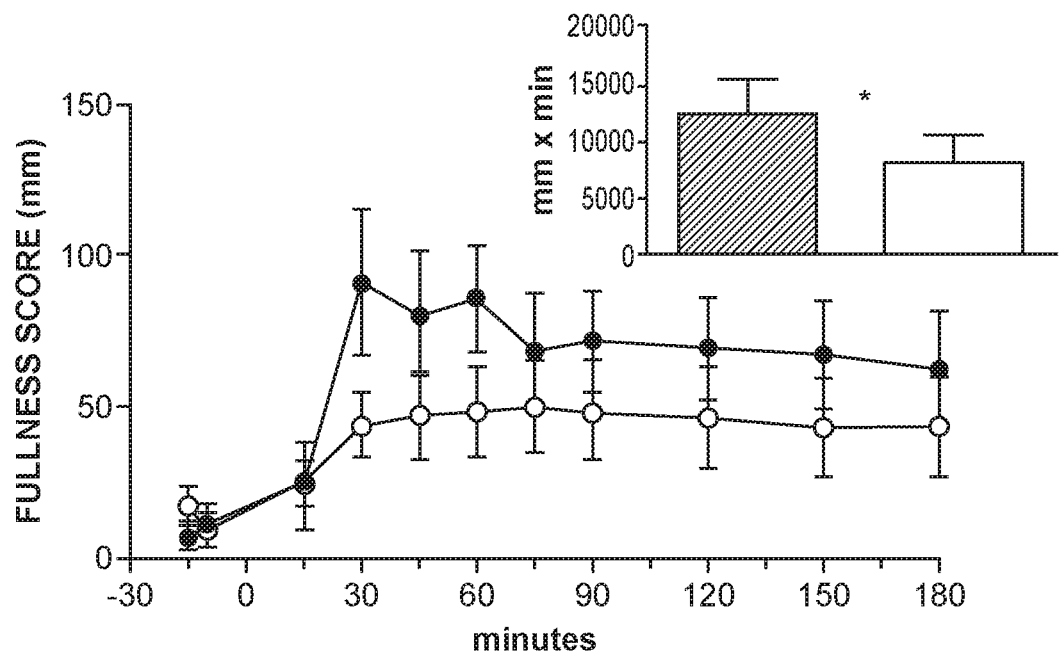
FIG. 2 shows the satiety response in a proof-of-concept human tube-feeding study.
Figure 3A:
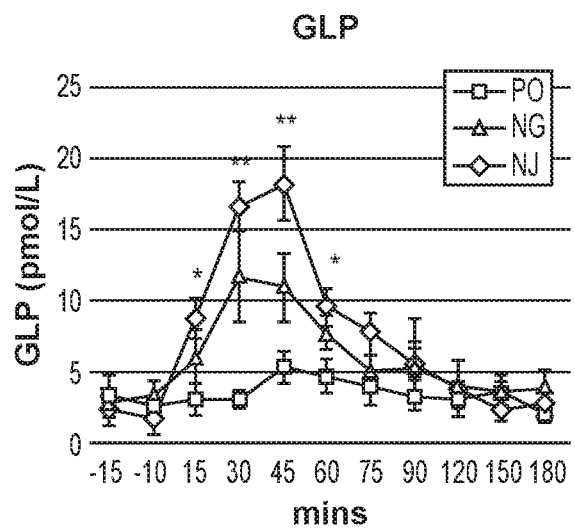
FIG. 3 shows the hormone response in a proof-of-concept tube feeding study conducted in adults with type 1 diabetes.
Figure 3B:
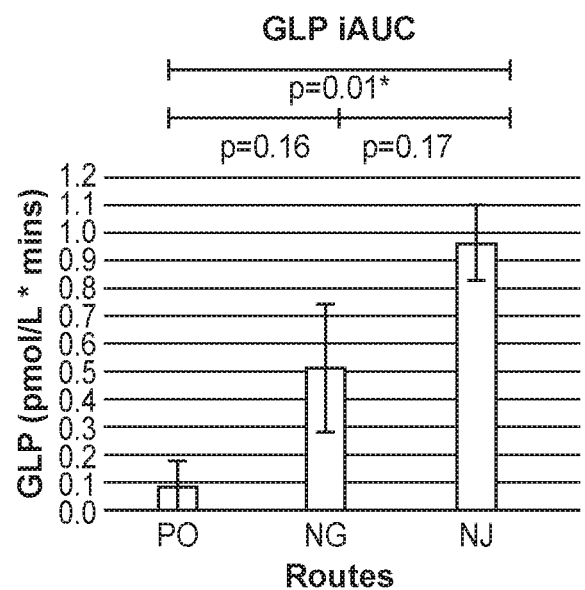
Figure 3C:
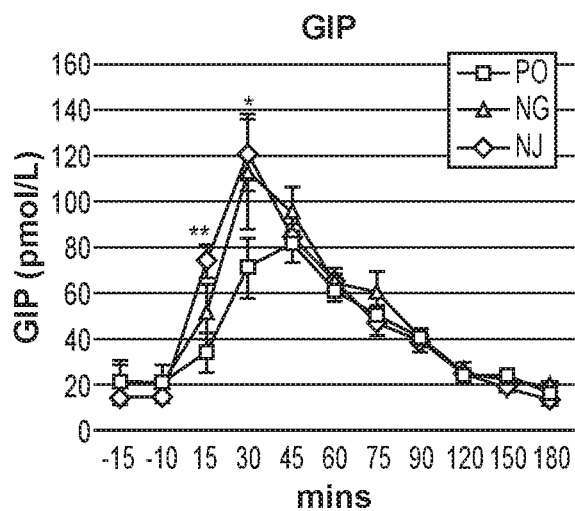
Figure 3D:
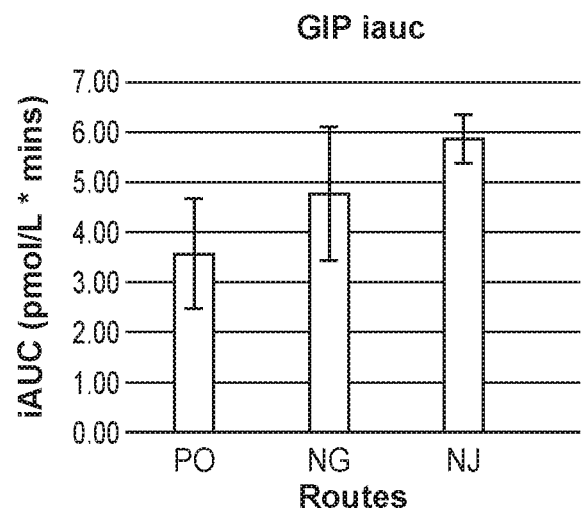
Figure 4A:
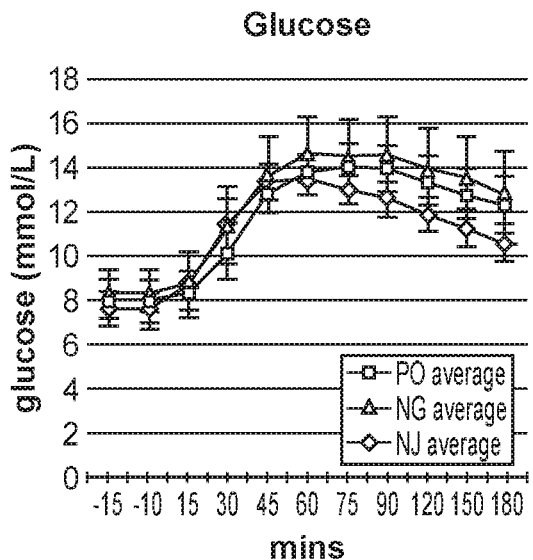
FIG. 4 shows the glucose response in a proof-of-concept tube feeding study conducted in adults with type 1 diabetes.
Figure 4B:
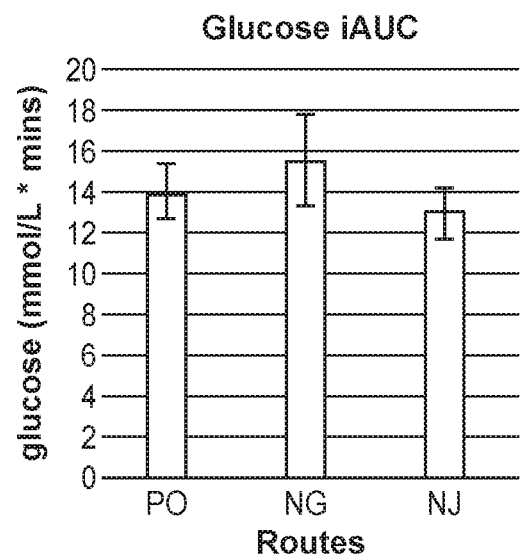
Figure 4C:
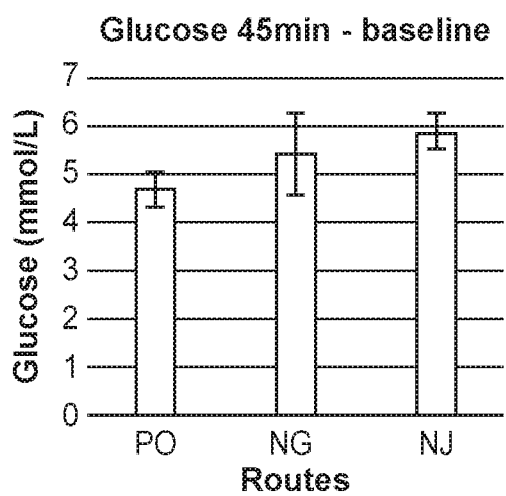
Figure 4D:
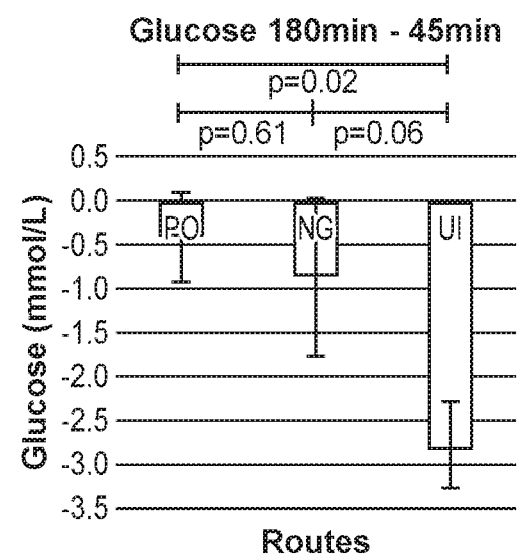

Obese adults with type 2 diabetes underwent paired three hour enteral and oral mixed meal tolerance tests via an enteral feeding tube as shown in FIG. 1. Seven participants received 125 kcal an uncoated mixed nutrient meal over 15 mins and seven 250 kcal over 30 minutes. GLP-1, PYY, insulin and glucose levels and symptoms scores were compared between routes, satiety level was also evaluated. See, FIGS. 1 and 2.

Enteral meals were associated with significantly higher levels of Glucagon-like peptide-1 (GLP-1 ref en.wikipedia.org/wiki/Glucagon-like_peptide-1), Peptide YY (PYY ref en.wikipedia.org/wiki/Peptide_YY and insulin than oral meals in a dose-dependent manner. The 250 kcal meal significantly increased measures of satiety, which were strongly correlated with levels of GLP-1 and PYY. Meals were generally well tolerated.

Experiment No. 2: Targeted Enteral Feeding Simulates Gastric Bypass (the FREE Study)

A similar study was conducted in adults with type 1 diabetes, and similar changes were observed in GLP-1 levels.

GLP-1 levels in the upper intestinal route were significantly higher than that in the gastric route only at 45 minutes (p=0.035). GLP-1 levels were not significantly different among routes after 45 minutes. The iAUC of GLP-1 was greatest for the upper intestinal route, intermediate for the gastric route, and least for the oral route, with difference between upper intestinal and oral routes reaching statistical significance (p=0.01, FIG. 1B). This difference likely corresponds to the marked difference in GLP-1 levels among the three routes from baseline up to 45 minutes. See, FIGS. 3 and 4.

Experiment No. 3: Ambulatory Tube-Feeding Human Study (the FREE TO GO Study)

This study evaluates whether repeated administration of oral uncoated mixed meal via enteral feeding tube to the upper intestine over a two week period can increase satiety, improve regulation of glucose, and promote weight loss.

Obese adults with type 2 diabetes underwent the study.

Figure 5:
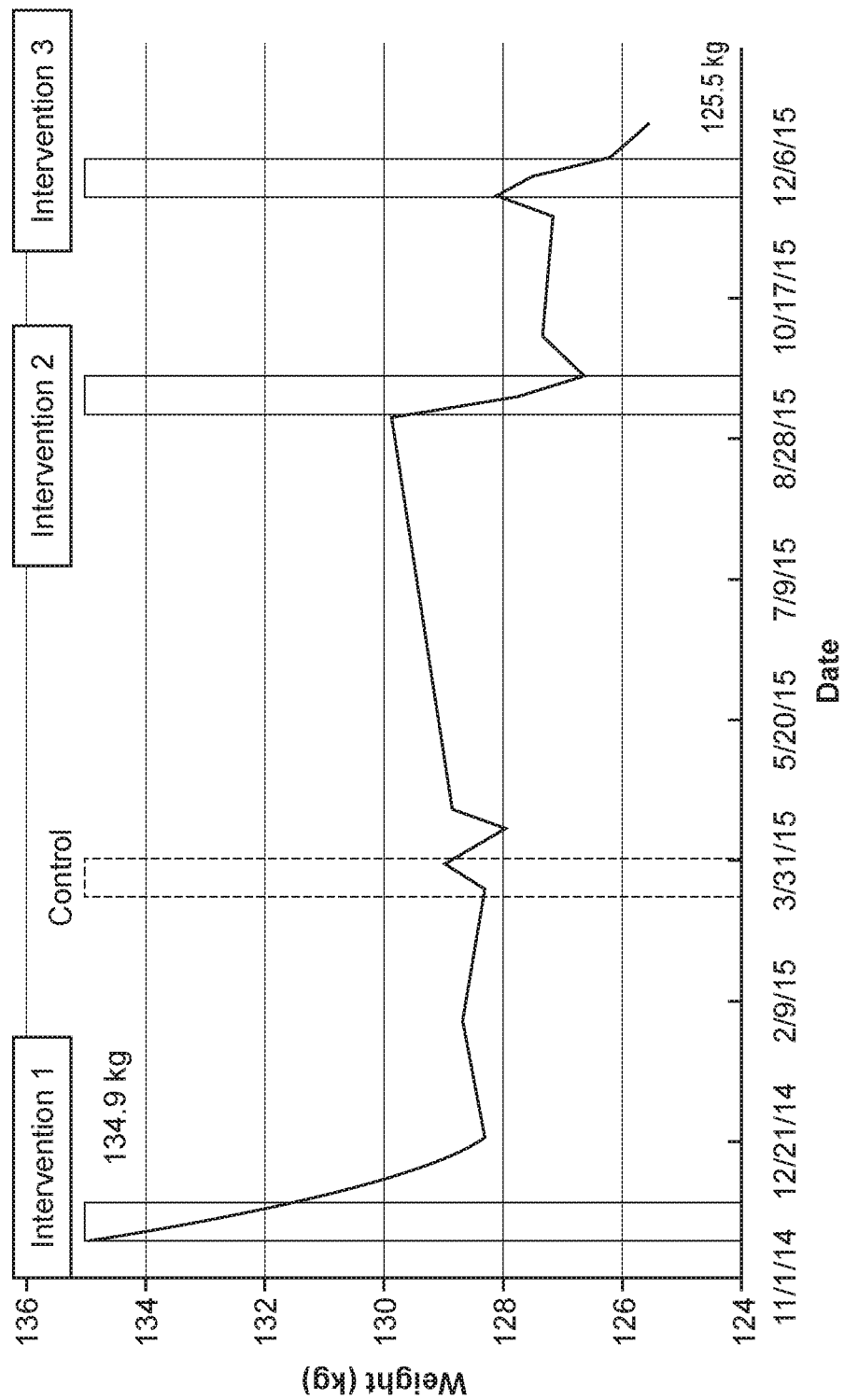
FIG. 5 depicts weight loss data in a proof-of-concept ambulatory tube-feeding human study.
Figure 6:
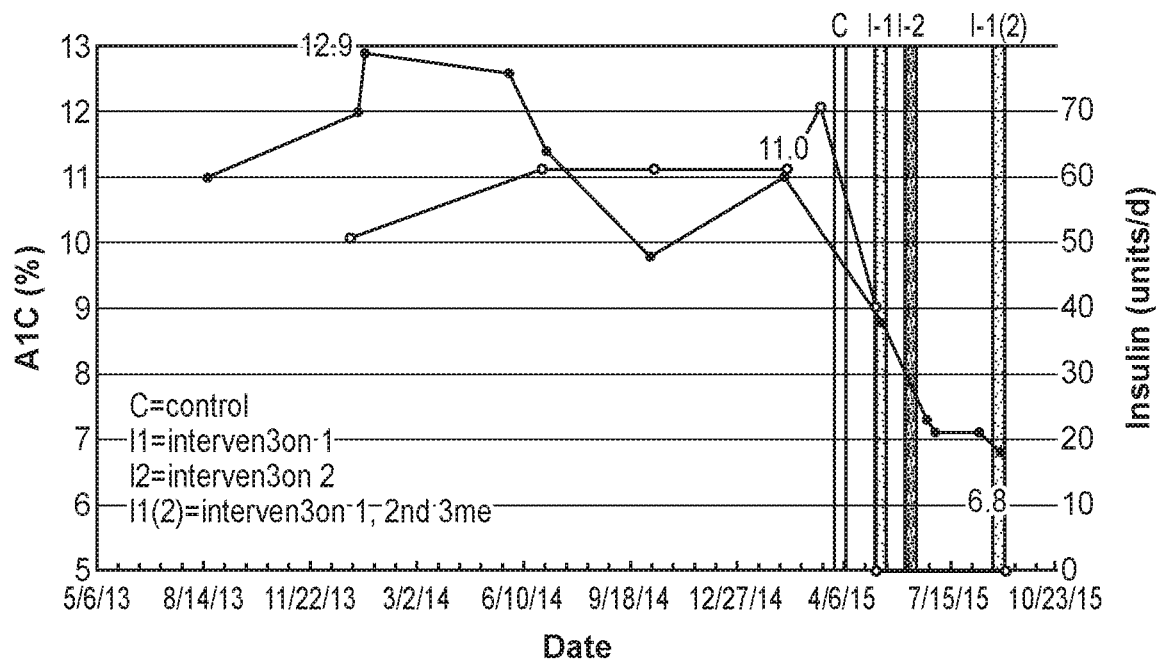
FIG. 6 depicts glucose-related data in a proof-of-concept ambulatory tube-feeding human study.

All participants reported increased satiety after administration of the mixed meal to the upper intestine; several experienced clinically significant weight loss, and some were able to discontinue insulin and decrease oral diabetes medication. See, FIGS. 5-6.

Experiment No. 4: Pre-Clinical Evaluation of Microparticle Formulations Sucrose and Nutrateric™ In Vitro Testing Suglets were coated with Nutrateric™ at Colorcon facilities using a Wurster Column. Subsequent curing was done at a private facility to improve stability at low pH.

Release of sucrose into buffer was measured with a refractometer.

Figure 7:
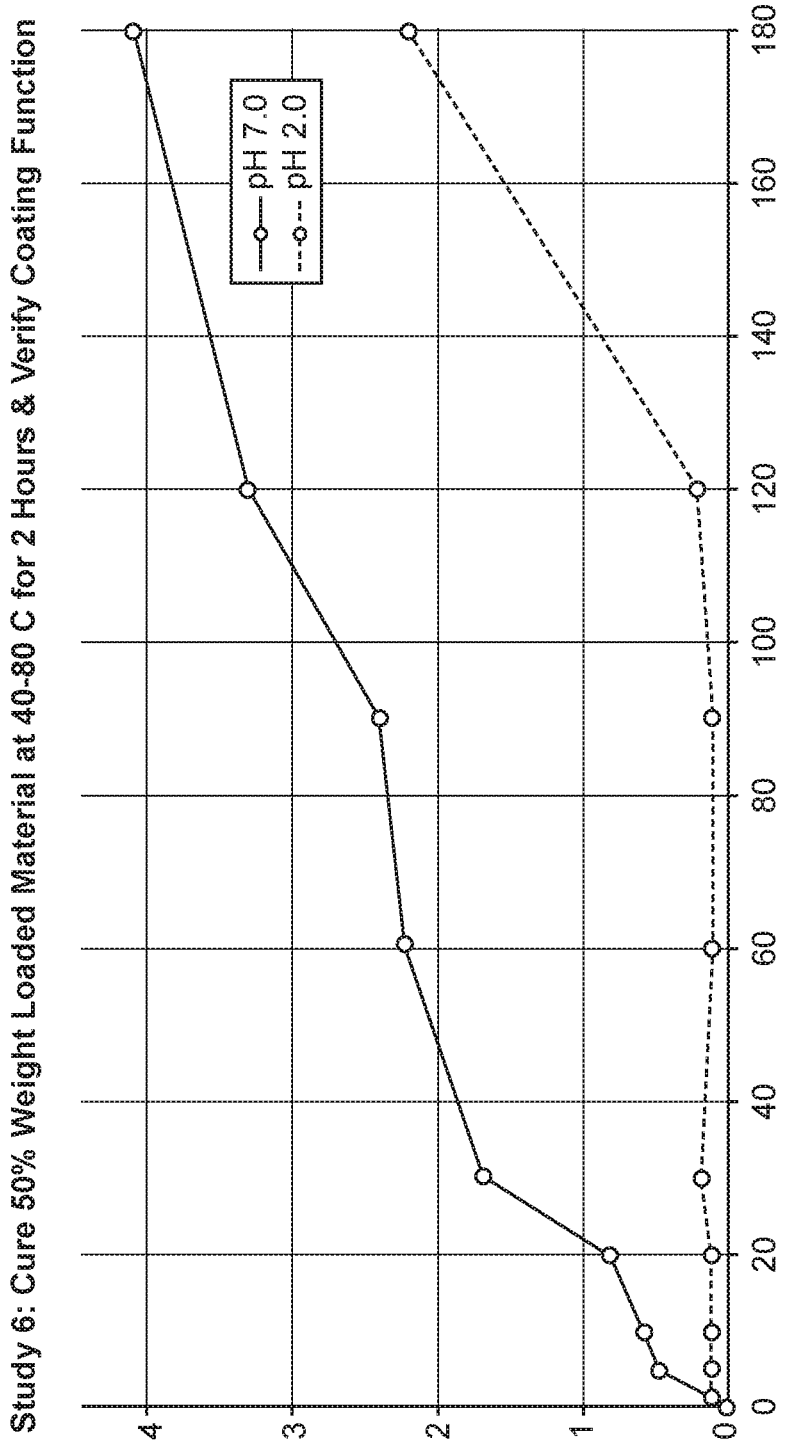
FIG. 7 depicts the sucrose release profile of Nutrateric™ coated sucrose at 2 pH levels.

It is demonstrated that the sucrose could be maintained in the coating at low pH and released at neutral pH with a specific coating level and appropriate processing. Steps were required to avoid presumed osmotic rupture of the particles. See, FIG. 7.

Sucrose and Nutrateric™ Human In Vivo Testing

This study evaluates the use of Nutrateric™ on sucrose. The Nutrateric™ was prepared at 10% solid and the recommended 85:15 Surlease® to NS Enteric®.

Figure 8:
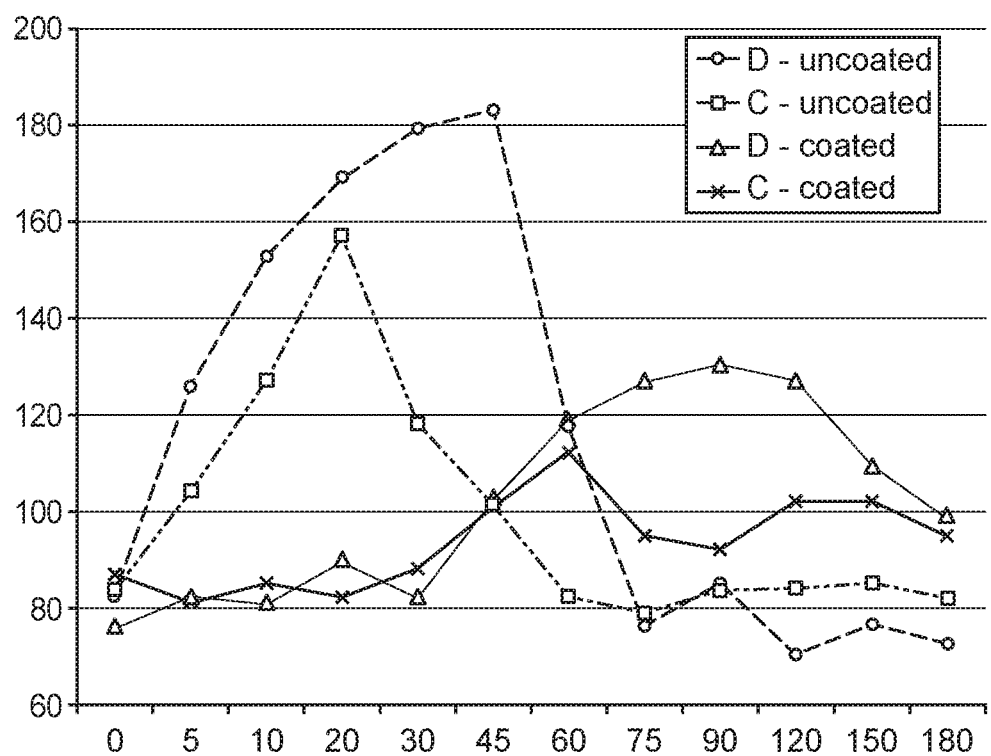
FIG. 8 depicts the blood glucose profile following ingestion of the microparticle having a Sucrose core and a Nutrateric™ coating.
Figure 9:
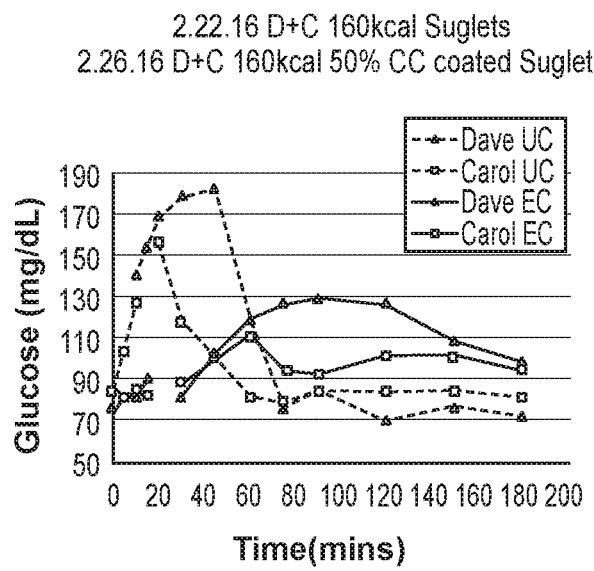
FIG. 9 depicts blood glucose satiety and side effects following ingestion of the microparticle having a Sucrose core and a Nutrateric™ coating.
Figure 9:
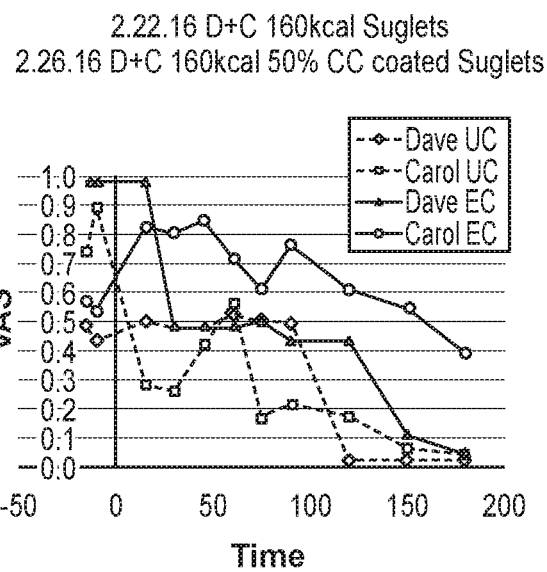
Figure 9:
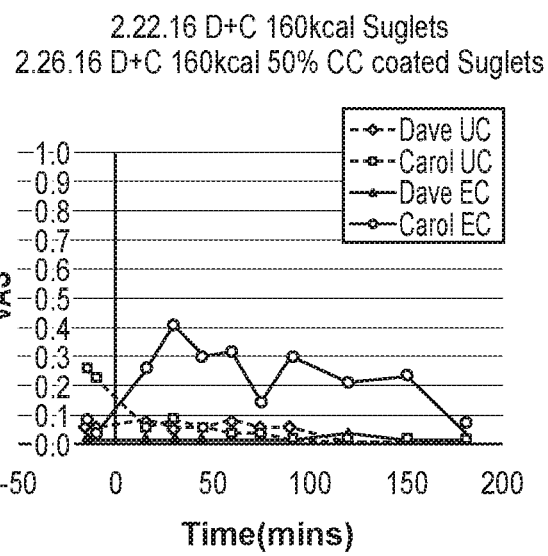
Figure 9:
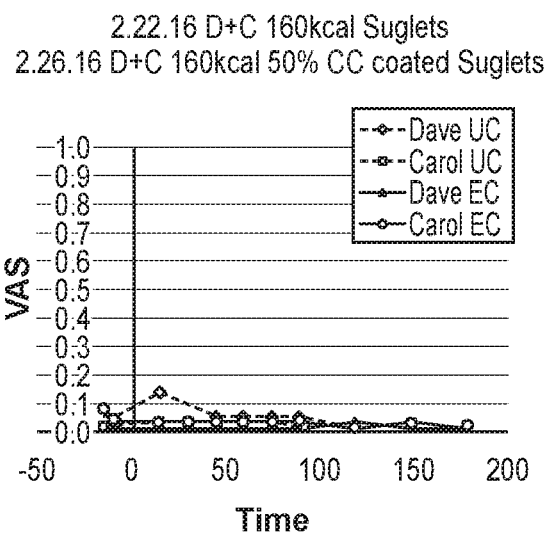
Figure 9:
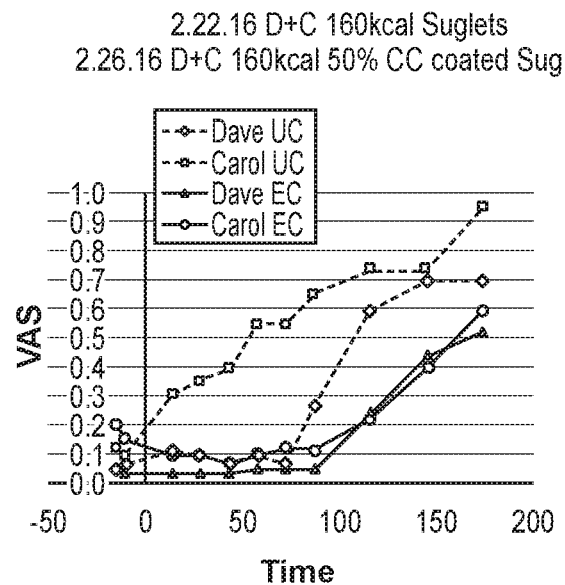
Figure 9:
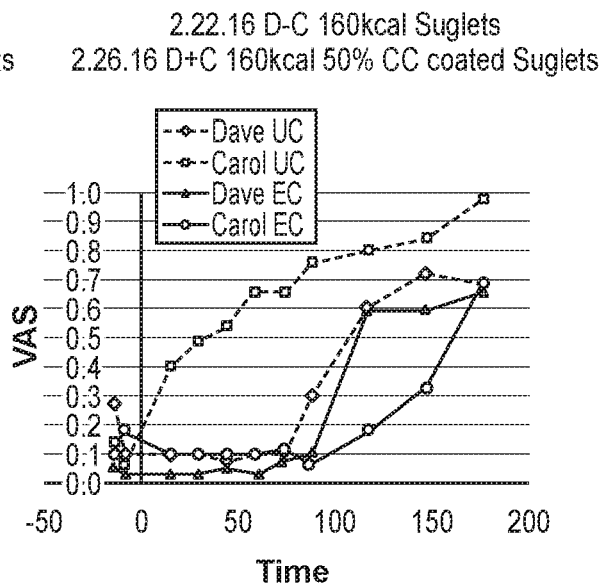
Figure 9:
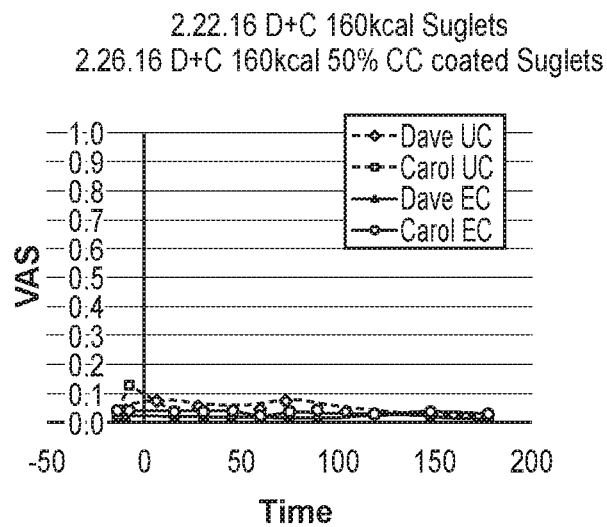
Figure 9:
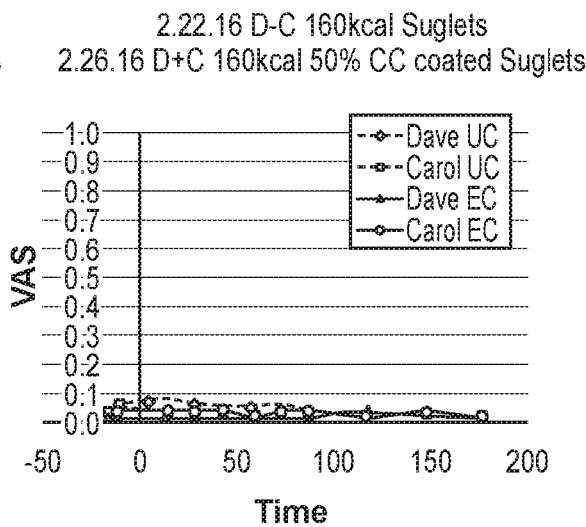

Coated and uncoated sucrose was ingested by 2 human adult research volunteers. Blood glucose was checked to monitor absorption of glucose derived from ingested sucrose. This demonstrated that the coated sucrose was associated with a delayed rise in blood glucose relative to the uncoated sucrose that can be attributed to effective enteric coating of the sucrose. See, FIG. 8 with time in minutes on x axis and blood glucose level in mg/dl on y axis. FIG. 9 demonstrates that in this experiment the coated sucrose was associated with greater satiety (greater fullness, less desire to eat and hunger) than the uncoated sucrose as well as non-significant pain, palpitations and perspiration and mild transient nausea in 1 subject. In FIG. 9, EC refers to enteric coated nutrient, and UC referes to uncoated nutrient. The x axis is time in minutes and the y axis, apart from glucose, represents scores on a visual analog scale.

Whole Milk Powder/Sugar Spheres and Eudraguard Natural™

Two different macronutrients, whole milk power and sugar spheres, can be separately coated and also jointly coated with an enteric coating with EUDRAGUARD® Natural (GRAS).

Nutraceutical layering is performed in a fluid bed coating system with two different sizes of sugar spheres: 18/20 mesh (850-1000 μm) and 16/18 mesh (1000-1180 μm).

Based on the surface area of the sugar spheres, the targeted total weight gain of EUDRAGUARD® Natural is calculated. One batch of EUDRAGUARD® Natural standard formulation is manufactured to target minimal release (less than 20%) at pH 1.2 for 2 hours, and the other is manufactured for full release (at least 80%) at pH 6.5 over 3 hours.

In the combined version a Suglet® sugar sphere "seed" (particle size 180-250 microns) is spray-coated with optimized whole milk powder macronutrient solution to form the macronutrient core. It is anticipated that the macronutrient powder will have an approximate diameter of about 1 mm.

The macronutrient core is further enteric coated with EUDRAGUARD® Natural at no more than about 15% to about 20% coating level.

Optimal formulations of the enteric coating are determined by adding a water soluble pigment to the formulation, and testing the coated microparticles for visual observation of pigment release in a dissolution bath at pH 1.2 (2 hrs) followed by phosphate buffer pH 6.8. The formulations can be tested by fiber optic dissolution (based on water soluble dye) at desired pH level. A release profile over 3 hours is generated to aid in the optimal formulation release characteristics.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A microparticle comprising a nutrient-filled core encapsulated in an enteric coating comprising one or more layers that comprise an alginate and a starch acetate and wherein the core comprises at least one macronutrient and optionally one or more micronutrients, excipients, hydrogels, bile acids, probiotics, and/or preservatives, and optionally wherein the at least one macronutrient comprises one or more of a protein, a carbohydrate, Ensure®, whole milk powder, sucrose, sugar spheres, and a lipid and the core comprises one or more layers and at least one of a whey protein, a soy protein, and a pea protein; and wherein the one or more micronutrient comprises at least one ion selected from the group consisting of iron, cobalt, chromium, copper, iodine, manganese, selenium, zinc, molybdenum, calcium, sodium, chloride, magnesium, potassium, and/or any combination thereof.

2. The microparticle of claim 1, wherein the enteric coating further comprises one or more of a resistant starch, gelatin, cellulose, modified cellulose, chitin, a methacrylic acid copolymer a shellac, a carboxymethylcellulose, EUDRAGUARD® Natural, Nutrateric® Nutritional Enteric Coating System, insoluble fibers, and/or any combination of these polymers with or without other materials.

3. The microparticle of claim 1, further comprising at least one of minerals, vitamins, fiber, bile acids, probiotics, prebiotics, flavoring agents, coloring agents, excipients, hydrogel, preservatives, and/or any combination thereof.

4. The microparticle of claim 1, wherein the enteric coating is configured to be dissolved in an upper intestine of an individual.

5. The microparticle of claim 1, wherein the enteric coating is configured to be dissolved at a pH of about 6.5 or above and not substantially dissolved at a pH of about 3.5 or below.

6. A method for delivering nutrients directly to an upper intestine of an individual, the method comprising administering to the upper intestine an effective amount of the microparticle of claim 1.

7. The method of claim 6, wherein the method is used in conjunction with at least one weight loss or blood glucose control strategy comprising a gastric band, a intragastric balloon, anti-diabetic medication, and weight loss medication.

8. The method of claim 6, further comprising measuring a glucose level, and adjusting the effective amount to the individual based on the measured glucose level.

9. A kit comprising the microparticle of claim 1, a carrier, and instructions for use to an individual.

10. The microparticle of claim 1, wherein the enteric coating further comprises a macronutrient.

11. The microparticle of claim 1, wherein the thickness of the enteric coating is non-uniform.

* * * * *